United States Patent [19]

Kruger

[11] 4,134,891

[45] Jan. 16, 1979

[54] 14-FUNCTIONALIZED 8,19-OXIDO STEROIDS AND PROCESSES FOR PREPARATION THEREOF

[75] Inventor: Gunther Kruger, St. Laurent, Canada

[73] Assignee: Steele Chemicals Co. Ltd., Quebec, Canada

[21] Appl. No.: 710,696

[22] Filed: Aug. 2, 1976

Related U.S. Application Data

[63] Continuation-in-part of Ser. No. 497,729, Aug. 15, 1974, abandoned, which is a continuation-in-part of Ser. No. 215,669, Jan. 5, 1972, Pat. No. 3,849,402.

[30] Foreign Application Priority Data

Jan. 4, 1972 [CA] Canada .................................. 131672

[51] Int. Cl.$^2$ ......................... C07J 71/00; C07J 19/00

[52] U.S. Cl. ...................... 260/239.55 R; 260/239.57
[58] Field of Search .............................. 260/239.55 R

[56] References Cited

U.S. PATENT DOCUMENTS 3,849,402  11/1974  Kruger ........................... 260/239.55

*Primary Examiner*—Elbert L. Roberts

[57] ABSTRACT

There are provided novel 14-functionalized 8,19-oxido steroids possessing 14α or 14β-hydroxy, 14α and 14β-acetoxy, 14α,15α-oxido or 14β,15β-oxido groups or a double bond in position 14 as well as processes for preparing such compounds. These compounds can be readily converted into the corresponding 14β-hydroxycardenolides, 19-oxygenated cardenolides, 19-norcardenolides and unsaturated cardenolides.

89 Claims, No Drawings

14-FUNCTIONALIZED 8,19-OXIDO STEROIDS AND PROCESSES FOR PREPARATION THEREOF

This application is a c-i-p of Ser. No. 497,729, filed Aug. 15, 1974 now abandoned, which is a c-i-p of Ser. No. 215,669 filed Jan. 5, 1972 (now U.S. Pat. No. 3,849,402).

This invention relates to steroid compounds.

More particularly, one aspect of this invention relates to processes for the preparation of 14-functionalized 8,19-oxido steroids possessing 14α or 14β-hydroxy, 14α and 14β-acetoxy, 14α,15α-oxido or 14β,15β-oxido groups or a double bond in position 14. In a still further aspect of this invention, there are provided novel compounds of the type just mentioned, as described hereinafter in greater detail.

The prior art in the field of this invention is quite limited. In brief summation of the prior art, there are known compounds, which are only of academic interest for which no other utility could be ascertained and which are of the following formula:

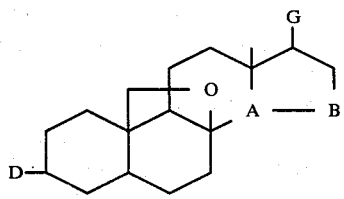

wherein D and G are the same as Y and R in Formula I, respectively, as defined hereinafter, and A and B are non-functionalized 14- and 15-carbon atoms carrying one or two hydrogen atoms, respectively. Likewise, known compounds include (and which again had been prepared only for academic interest) compounds of the above formula where A and B represent 14- and 15-carbon atoms linked by a double bond and wherein G is the same as D and both are =O; or wherein G is the same as D and both are O—CH₂—CH₂—O; other compounds being those where G is CHOAc—CH₃ when D is —OAc as well as those where G is CO—CH₃ and D is =O. Such compounds are described in D. Hauser et al, Helv., 47, 1961 (1964). This prior art, as will be seen from a review of this reference, yields the above compounds only in very inferior yields and admixed with other products. The separation of the by-products is very difficult and, can only be achieved by chromatography, so that such processes are not suitable for the preparation of large amounts of end products. In contrast, the novel processes of the present invention overcome the disadvantages of the prior art, as will be seen from the subsequent detailed description. Still further, there are provided new compounds which are more effective to those of the prior art as described above.

More particularly, the products of the present invention are those compounds having the formula

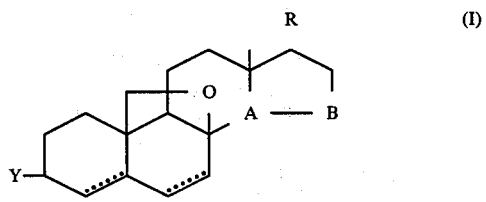

wherein Y is selected from the group consisting of α-OH, β-OH, H, =O, O—acyl and tetrahydropyranyloxy; A and B may represent functionalized 14- or 15-carbon atoms, respectively, which are either linked by a double bond, or which carry an α- or β-oxido or a 14α- or 14β-hydroxy group, in which case B is a methylene group; the compounds have an optional double bond in position 4(5), and/or 6(7); in the case of the 5-position being saturated, the 5-hydrogen atom is either in the α-or β-position; and R is selected from the group consisting of O—Z;

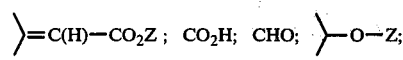

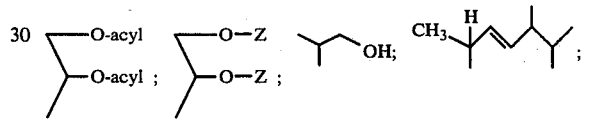

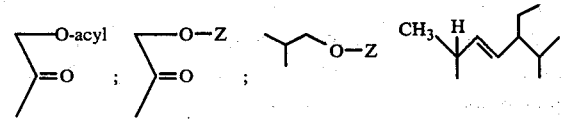

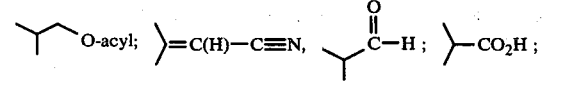

and CN, wherein Z represents tetrahydropyranyl or lower alkyl, preferably methyl, or a substituted methyl, wherein the substituent is selected from the group consisting of phenyl, halogen, preferably chlorine and bromine, methoxy, $CH_2=CH$ and $HC\equiv C$; acyl represents a group selected from those consisting of acetate, tri-lower-alkyl acetates, wherein the lower alkyl group is preferably methyl or ethyl, monohalo acetates and trihalo acetates, preferably wherein the halogen is chlorine and bromine.

In accordance with a further aspect of the present invention, there are also provided processes for preparing the above compounds, and in general, compounds of the Formula Ia

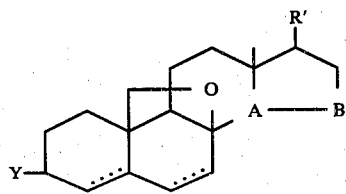
(Ia)

wherein Y, A and B are as defined above, and R' is selected from the group consisting of O-acyl or O-Z;

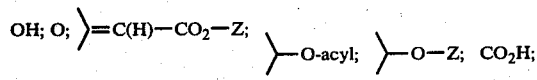
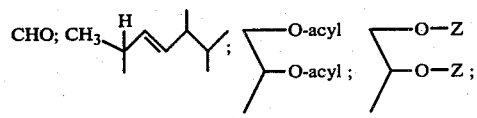
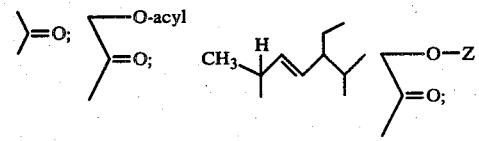
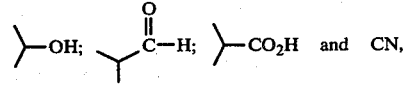
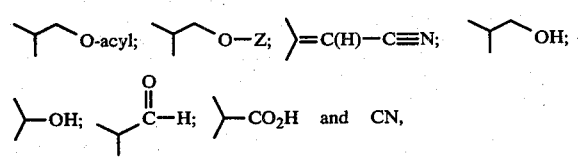

wherein Z and acyl are as defined above.

More particularly, in accordance with the process aspect of the present invention, the process for preparing compounds of the Formula I and Ia is selected from the group consisting of
(a) treating a compound of the Formula II

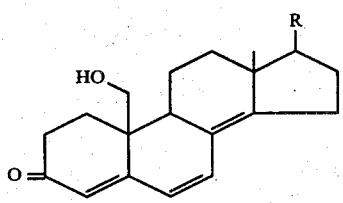
(II)

wherein R is as defined above, with a peracid, to form a mixture of compounds of the Formulae IIIa, IIIb or I, where Y' is O= and R is as defined above:

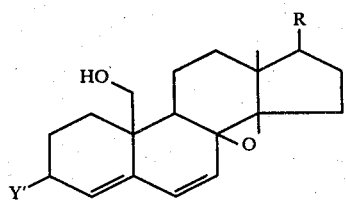
(IIIa)

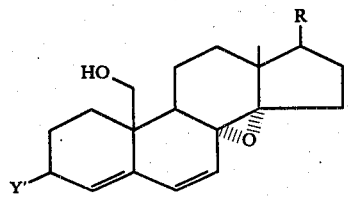
(IIIb)

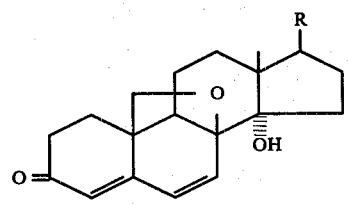
(I)

if desired, separating compound IIIa thus obtained from the above mixture and treating the latter compound with an acid to form a 14β-hydroxy-3-ketone of Formula I, as follows:

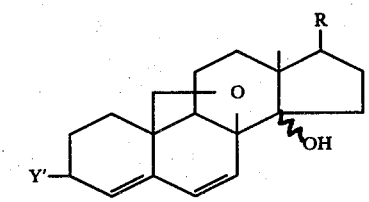
(I)

where Y' is OH or O=; similarly separating the α-epoxide IIIb and treating it with an acid to form a 14α-hydroxy-3-ketone of the above formula I; optionally reducing 8β,14β-oxido- or 8α, 14α-oxido-4,6-dien-3-ones IIIa or IIIb to the corresponding 3-alcohols of the respective formulae IIIa or IIIb, Y' being OH, and subsequently subjecting the latter 8,14-oxides to acid treatment to form the respective 3,14-β- and 3,14α-hydroxy-8,19-oxido-4,6-dienes of the above formula I;
(b) treating a compound of the Formula IV

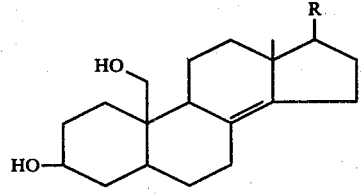
(IV)

wherein R is as defined above, with a peracid to form a mixture of compounds of the formulae

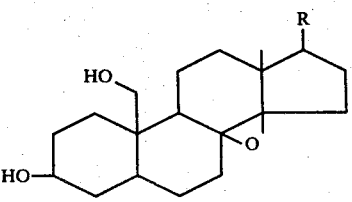
(V)

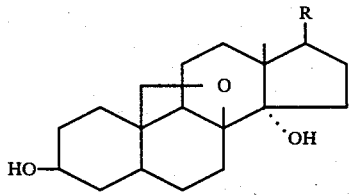

in which R is as defined above; if desired, separating from said mixture said compound of said Formula V, and treating said compound of Formula V under catalytic hydrogenation conditions or with an acid to form a compound of the Formula I as follows:

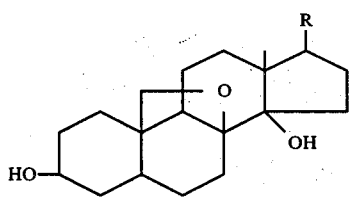

(I)

(c) epoxidizing a compound of the Formula

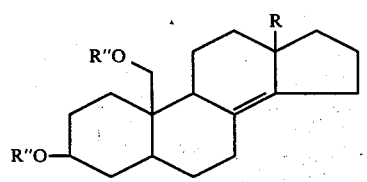

(VI)

wherein R is as defined above and R'' is acyl, preferably O=C—H, O=C—Cl, O=C—CH₃, O=C—CH₂ halogen, O=C—CH(halogen)₂, O=C—C(halogen)₃, O=C—C(CH₃)₃, O=C—O—CH₂-phenyl, O=C—O—C(CH₃)₃, into a mixture of compounds of the Formulae VII and VIII

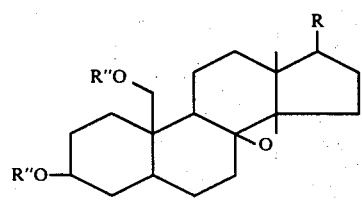

(VII)

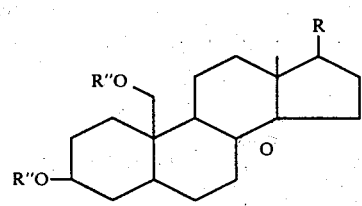

(VIII)

in which R' and R'' are as defined above, separating from said mixture said compounds VII and VIII, and, in the case of the compound of the Formula VII, treating the latter with a base to form the compound of the Formula V and subsequently subjecting the latter to acid or hydrogenation conditions to form a compound of the Formula I as follows:

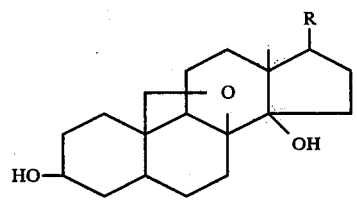

in the case of the compound of the Formula VIII, subjecting the latter to successive base-acid treatment to yield a compound of Formula:

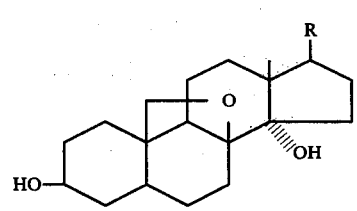

(I)

(d) epoxidizing a compound of the Formula IX

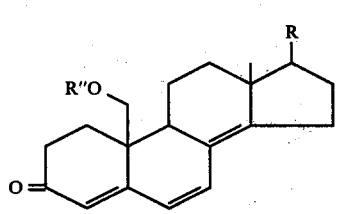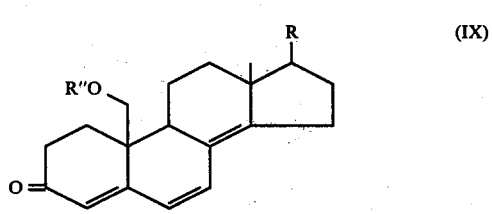

(IX)

wherein R'' is as defined above to form a compound of the Formula X

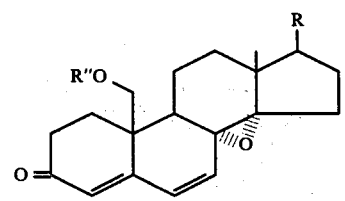

(X)

wherein R and R'' are as defined above; and treating the latter compound with a base and then with an acid to form a compound of the Formula I, as follows:

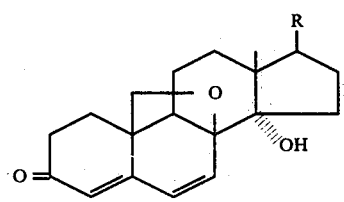

(e) oxidizing a compound of the Formula XI

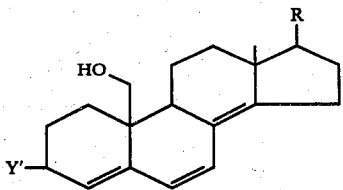

wherein R is as defined above and Y' is OH or O=, to form a compound of the Formula I as follows

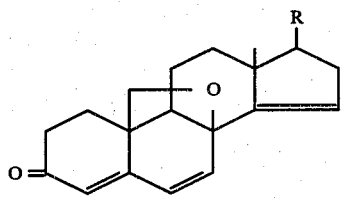

and (f) oxidizing a compound of the Formula XII

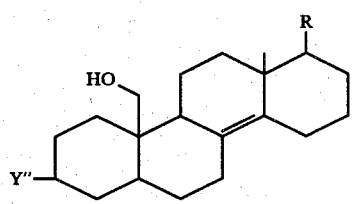

wherein R is as defined above and Y" is OH, O—acyl or =O to form a compound of the Formula I as follows:

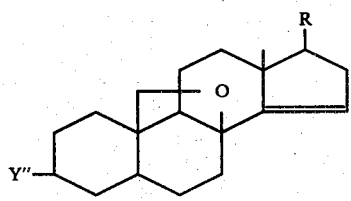

(g) epoxidizing a compound of the Formula XV

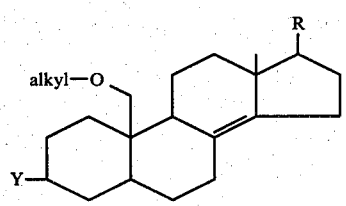

wherein Y and R are as defined above, and alkyl is preferably tetrahydropyranyl, benzyl, allyl and propargyl, into a compound of Formula XVI

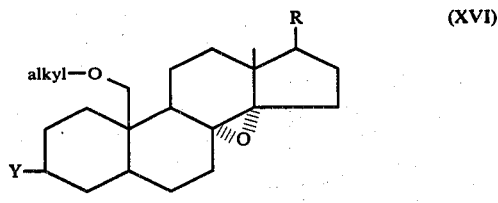

and subsequently subjecting the latter to hydrogenation conditions to form a compound of Formula I as follows:

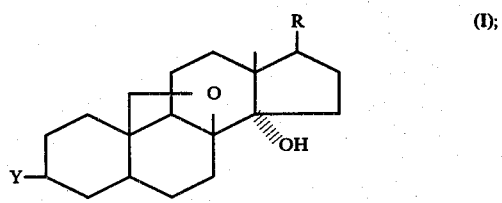

wherein Y and R are as defined above, (h) epoxidizing a compound of Formula XVII

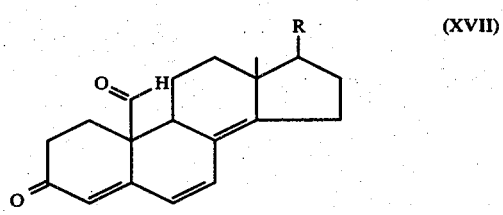

wherein R is as defined above, into a compound of Formula XVIII

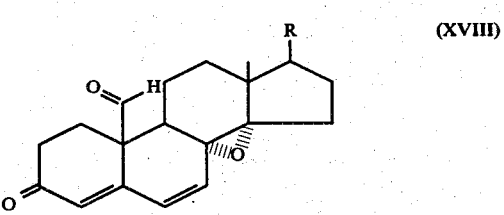

and subsequently subjecting the latter to reducing conditions to form a compound of Formula I as follows:

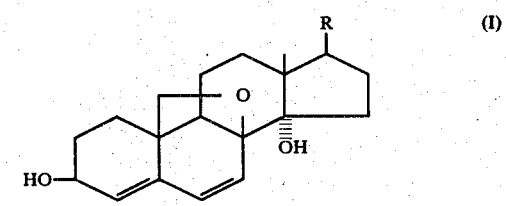

wherein R is as defined above.

Particularly preferred compounds of the present invention are those compounds of the formula:

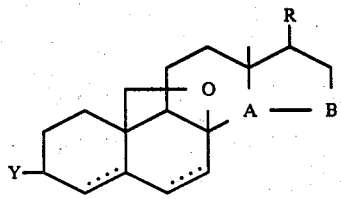

wherein Y is selected from the group consisting of α-OH, β-OH, H, =O, O—acyl and —O—tetrahydropyranyl; A and B represent 14-and 15-carbon atoms, respectively, which are either linked by a double bond or an α-oxido bridge or have a hydroxy group, or acetoxy group or halogen atom in the 14β- or 14α-positions, in which case B is a methylene group; the dotted lines represent optional double bonds in position 4(5), and/or 6(7); in the case of the 5-position being saturated, the 5-hydrogen atom is either in the α or β-position; and R is selected from the group consisting of

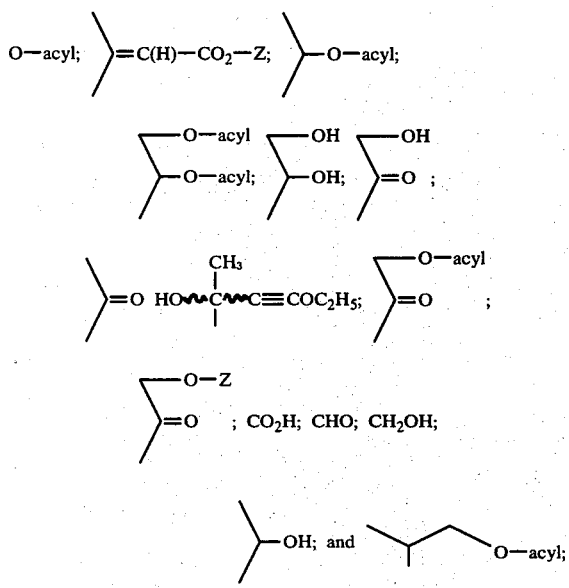

wherein Z is tetrahydropyranyl, lower alkyl, or a substituted methyl, wherein the substituent is selected from the group consisting of phenyl, halogen, methoxy, $CH_2=CH$ and $HC\equiv C$; acyl represents a group selected from those consisting of formyl, acetyl, tri-lower-alkyl acetyls, wherein the lower alkyl group is methyl or ethyl, monohalo acetyls and trihalo acetyls, and in the case of AB-ring saturated 8,19-oxido 5α- and 5β-androst-14-enes and AB-ring saturated 21-unsubstituted 8,19-oxido 5α-pregn-14-enes, Y is H only.

Particularly preferred compounds of the present invention are those compounds where, in the above formula, R is selected from the group consisting of

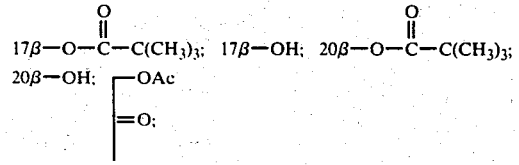

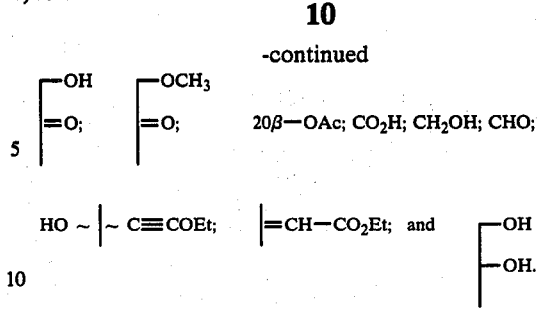

Also preferred within the above formula are compounds where Y is hydrogen, hydroxy or keto and particularly preferred compounds are where R is a member of the aforementioned preferred group with Y being chosen from the group of hydroxy, hydrogen or keto.

A preferred process of the present invention comprises a process of preparing a compound of the formula

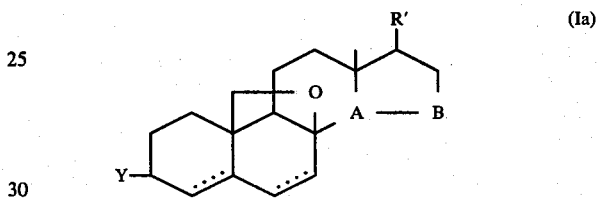

wherein Y, A and B are as defined above, and R' is selected from the group consisting of O—acyl; O—Z; OH; O;

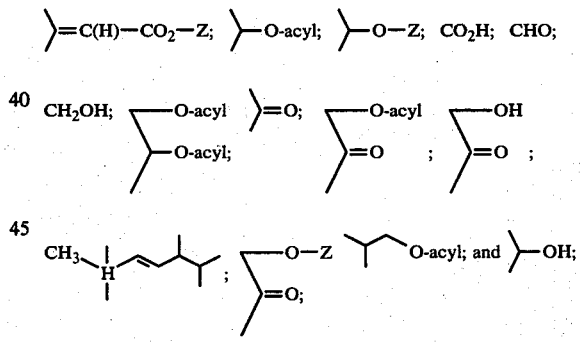

wherein Z and acyl are as defined above, which process comprises:

(a) treating a 19-hydroxy-8(14)-ene compound of the formula

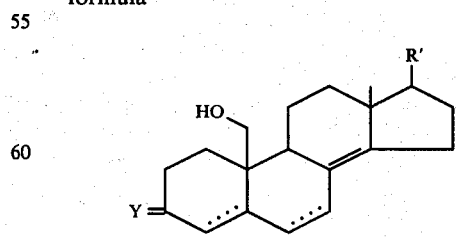

wherein Y, R' and the dotted lines represent optional double bonds in position 4(5), and/or 6(7), with a peracid to form a mixture of the Formulae IIIa, IIIb and I

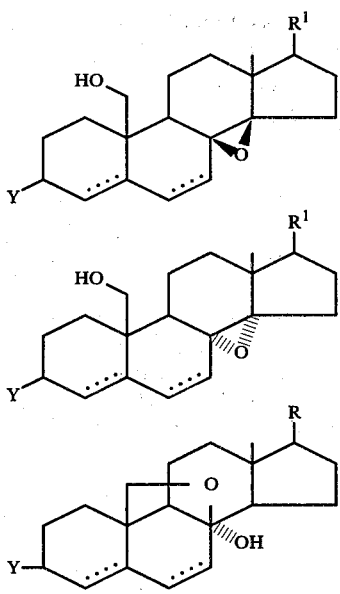

(b) and treating the compounds IIIa or IIIb with an acid to form a 14β or a 14α-hydroxy-8,19-oxide of Formula I below

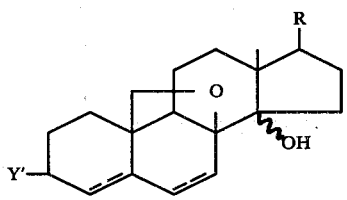

where the wavy line indicates that the 14-hydroxy is either in the β- or α-position.

In greater detail, and referring initially to process (a), the initial step of treating a compound of the Formula II with a peracid yields the mixture of 3-ketones of Formulae IIIa, IIIb and I as previously outlined. Amongst the solvents which may be used are those which include, for example, carbon tetrachloride, benzene, hexane, methanol, etc. Reaction temperatures may range from below to above room temperature as desired. The peracid employed in this reaction may be any suitable peracid for this purpose; typical examples being perbenzoic acid, metachloroperbenzoic acid, peracetic acid, etc. The resulting mixture of isomeric 8,14- and 8,19-oxides obtained may be separated and the isolated 8,14-oxides may then be treated with an acid to form the 14α and β -hydroxy compounds of Formula I. The optional reduction of the 3-ketones of Formulae IIIa or IIIb to the 3-alcohols IIIa or IIIb, respectively, may be carried out conventionally using a metal hydride in a suitable solvent, e.g. sodium borohydride in methanol. In carrying out the acid treatment step, a suitable carboxylic acid is preferably employed, such as, e.g. acetic acid, propionic acid, benzoic acid, etc. Alternately a dilute aqueous mineral acid may be employed. The acid treatment is carried out at temperatures ranging from 0° to 100° C. In the case of 8β,14β-oxido-4,6-dien-3-ones are reacted with a carboxylic acid the acid treatment is preferably carried out at elevated temperatures, e.g. at 70°; in all other cases it is carried out preferably at room temperature or below. If desired, a solvent may be employed if the particular acid used in the acid treatment is not a solvent per se; such additional solvents being, for example, carbon tetrachloride, ethyl acetate, benzene, toluene, etc.

The above-described embodiment (a) may be carried out in a one-step (i.e. as a "one-pot" reaction) if desired, without isolating a compound of the Formula III. Thus, a compound of the Formula II may be converted directly into a compound of the Formula I as and if desired. In a preferred embodiment of process (a), where it is desired to form essentially only the 8β,14β-oxide of Formula IIIa, it has been found that the solvent should be a non-polar solvent — e.g. hexane, carbon tetrachloride, etc.

The starting materials used in process (a), of the Formula II, can be obtained according to the teachings of copending Ser. No. 696,616 filed June 16, 1976, now issued as U.S. Pat. No. 4,058,539.

In process (b) the compounds of the Formula IV are reacted with a peracid, preferably under the reaction conditions described above with respect to process (a) and preferably using the same type of peracid described therein. The resulting reaction mixture contains a major amount of a compound of the Formula V, together with a minor amount of a compound of Formula I, as described above. If desired, the 14α-hydroxy compound of Formula I, and the 8β,14β-oxide of Formula V may be separated, whereafter the latter is then subjected to catalytic hydrogenation conditions which bring about a rearrangement to a compound of Formula I having a 14β-hydroxy group. To this end, conventional techniques and processes for catalytic hydrogenation may be employed, using for example, solvents such as acetic acid, propionic acid, methanol or ethanol, etc. and catalysts such as palladium or platinum.

In place of a catalytic hydrogenation rearrangement reaction, acid treatment of the compound of Formula V may be carried out to obtain the end product of Formula I described above. To this end, the acid treatment can be carried out using weak or strong acids; in the case of weak acids, the reaction is preferably carried out at elevated temperatures while in the case of strong acids, lower temperatures are employed. The weak acid may be any suitable acid such as, for example, boric acid, acetic acid, propionic acid, etc. which are employed at higher concentrations compared to the case where a strong acid is employed. Typical strong acids include, for example, para-toluenesulfonic acid, methanesulfonic acid, hydrochloric acid, sulphuric acid, etc. The strong acids are employed in the form of their dilute aqueous solutions. A particularly preferred embodiment of this process involves the use of 90% formic acid, which is a moderately strong acid, at room temperature. If desired, a solvent may be employed if the acid used does not function as a solvent. The solvent may be any suitable inert solvent, such as carbon tetrachloride, ethylacetate, benzene, toluene, etc.

The starting material of Formula IV used in process (b) may be obtained according to the teachings of copending application Ser. No. 215,669, filed Jan. 5, 1972, now U.S. Pat. No. 3,849,402.

With reference to process (c), the step of epoxidizing a compound of the Formula VI into a mixture of the compounds of Formulae VII and VIII, is carried out by using a peracid. In this respect, the peracid is described with respect to process (a) above, and the reaction conditions as to solvents, temperatures, etc. thereof may be used in the epoxidizing reaction of process (c).

The mixture of compounds of Formulae VII and VIII may then be subjected to hydrolysis conditions, e.g. basic conditions to yield initially a mixture of the corresponding 3,19-diols. In the hydrolysis bases such as potassium hydroxide, sodium hydroxide and solvents such as methane or other alcohols may be used. The 3,19-dihydroxy groups may also be formed by treatment of the corresponding acylates, which were used as starting materials, with metal hydrides in insert solvents, e.g. with sodium bis(2-methoxyethoxy)aluminium hydride in benzene. In the case of the initially formed 3,19-dihydroxy-8α,14α-oxide, it has been found that this compound has a tendency to cyclize spontaneously under hydrolysis conditions to directly form the end product. However, if desired, one can ensure completion of the reaction by mild acid treatment. Using either weak or strong acids the treatment may be carried out at room temperature or below. In the case of weak acids the treatment may be carried out with a co-solvent, in the case of strong acids, dilute aqueous solutions may be employed. Subsequent separation of the hydrolysis products yields then the 3,14α-dihydroxy-8,19-oxide (I) and 3,19-dihydroxy-8β,14β-oxide V, the cyclisation of which to the 14β-hydroxy-8,19-oxide of formula I may be carried out under hydrogenation conditions as described above for process (b).

The starting materials of process (c) may be obtained according to the teachings of copending application Ser. No. 215,669 filed Jan. 5, 1972, now issued as U.S. Pat. No. 3,849,402.

In process (d), a compound of the Formula IX is subjected to an oxidizing reaction using a peracid. Most preferably, the conditions employed in this embodiment are the same as those as defined above with respect to process (a), using the same general type of peracid. Likewise, optionally, a solvent may be present. The compound thus obtained, of Formula X, is then hydrolyzed yielding by concomitant cyclisation of the corresponding intermediate 19-hydroxy-8α,14α-oxide a compound of the Formula I, as outlined above. The hydrolysis reaction preferably is carried out using a base and an alcohol; typical of such bases which may be employed are potassium hydroxide, sodium hydroxide, sodium carbonate, etc. The alcohols which may be used include methanol, ethanol, propanol, etc. As in process (c) cyclisation of the 19-hydroxy 8α,14α-oxide formed after the base hydrolysis may be brought to completion by subsequent mild acid treatment.

The starting materials used in this reaction, Formula IX, may be obtained according to the teachings of copending application Ser. No. 215,669 filed January 5, 1972, now issued as U.S. Pat. No. 3,849,402.

In process (e), a compound of the Formula XI is converted directly into a compound of the Formula I, under oxidizing conditions. These oxidizing conditions using, for example, lead tetraacetate, activated manganese dioxide, or the like preferably in the presence of an inert solvent such as carbon tetrachloride, ether, or the like.

The starting materials used in process (e) may be obtained by the procedures described in copending applications Ser. No. 215,669 now issued as U.S. Pat. No. 3,849,402.

Referring now to process (f), and in one embodiment thereof, the compound of Formula XII is oxidized directly to form a compound of the Formula I as defined above with respect to this process. To this end, the reaction conditions are preferably similar to those with respect to process (e) described above; still further, other agents such as pyridinium hydrobromide perbromide, or bromosuccinamide in pyridine, and the like may also be employed.

In an optional embodiment of process (f), the compound of Formula XII may be initially halogenated in the 14-position to form a compound of the Formula

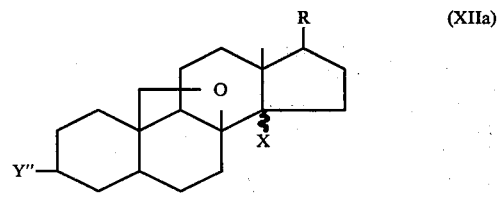

In carrying out this halogenation step, the reaction (depending on the halogen) may be accomplished using e.g. bromine in the presence of an inert solvent. Typical inert solvents include ether, etc. The product obtained of Formula XIIa may then be converted into a compound of the Formula I by subjecting the latter to base treatment, preferably in the presence of an inert solvent. For example, base treatment may be carried out using a mild base such as an alkali metal base, in the presence of pyridine or the like.

In process (g) a compound of Formula XV is subjected to epoxidation conditions using a peracid. Preferably, the conditions employed are those as defined above with respect to process (a). The 8α,14α-oxide of Formula XVI obtained is then subjected to the hydrogenation conditions as defined with respect to process (b) to yield the 8,19-oxido-14α-ols of Formula I. In the case where alkyl is tetrahydropyranyl the treatment under hydrogenation conditions may preferably be carried out in the presence of a weak carboxylic acid such as acetic acid.

In process (h) a compound of Formula XVII is subjected to epoxidizing conditions using a peracid. Most preferably, the conditions employed are those as defined with respect to process (a). The 8α,14α-oxide of Formula XVIII is then reduced with a metal hydride in a suitable solvent, e.g. with sodium borohydride in methanol, to yield the 3β,14α-dihydroxy-8,19-oxide of Formula I.

The various products obtained from the above-described processes (a) through (e) may be converted, if desired, into other novel products of the present invention. Thus, for example, where the products obtained of Formula I have a 3-keto group, this group may be reduced to form the corresponding 3-hydroxy compound by subjecting the compound to a reduction reacting using, for example, sodium borohydride in the presence of an inert solvent such as methanol. For greater detail of such reduction reactions, reference may be had to Fieser & Fieser Reagents for Organic Synthesis, 1967, page 1049. Likewise, where the end product of Formula I is unsaturated in the 4 and 6 position, the product may be hydrogenated using, for example, hydrogenation conditions involving palladium on charcoal in a hydrogen atmosphere — for greater detail, reference may be had to Fieser & Fieser (supra) page 778. In this respect, it has been found that when the 3-keto group reduction process is carried out before the 4,6-hydrogenation process more of the corresponding 5α-hydrogen steroids of Formula I will be obtained while when the reduction of the 3-keto group is carried out subsequently to the hydrogenation of the double bonds in the 4,6 position conversely, more of the corresponding 5β-hydrogen steroids of the Formula I will be obtained.

In addition, the compounds of Formula I having a 14α-hydroxy group may be converted to compounds of Formula I having a double bond in the 14-position. To this end, the 14α-hydroxy compounds of Formula I may be treated with thionyl chloride in pyridine, as for example, described in Fieser and Fieser (supra) page 1084. In turn, when the substituents A and B represent carbon atoms 14 and 15 linked by a double bond, such compounds of Formula I may be converted to the corresponding 14β-hydroxy compounds according to, for example Fieser and Fieser, page 1083. To this end, briefly summarized, such 14-dehydrosteroids may be initially converted to the corresponding 14β-ol, 15α-bromo adducts by treatment with hypobromous acid following which the latter adduct is converted to the corresponding 14β,15β-epoxide by treatment with an alkali. The epoxide may then be hydrogenolysed by treatment with a metal hydride (such as aluminum hydride — see page 599 of Fieser and Fieser supra), or by catalytic hydrogenation.

In the case where the compounds of Formula I have a 14-hydroxy group the latter may be converted to a 14-acetoxy group using isopropenyl acetate in the presence of a strong acid e.g. para toluenesulfonic acid. In the case where the 14-alcohols used as starting materials possess a keto group, concomitant conversion to the corresponding enol acetate takes place.

The products of Formula I are valuable intermediates for the preparation of 14β-hydroxy cardenolides of the Formula

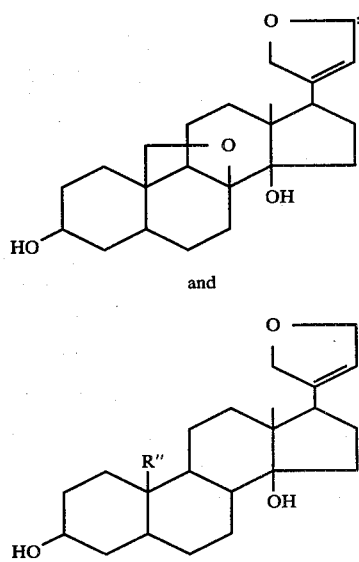

and wherein R" represents a 19-oxygenated group, such as CH₂OH and CHO, or a hydrogen atom. The conversion of the 14-functionalized 8,9-oxides of this invention to 14-functionalized 19-oxygenated and 10-hydrogen 8β and 8α-hydrogen analogs is described in copending patent application Ser. No. 497,730, filed Aug. 15. 1974.

The use of such compounds and their glycosides for the treatment of cardiac insufficiency is well known, as e.g. disclosed in Angewandte Chemie Vol. 9, no. 5, pp 321–332. Conventionally, such 14β-hydroxycardenolides have been isolated from natural sources. Recently a number of 14β-hydroxycardenolides have also been obtained by synthesis using 14β-hydroxy-pregnan-20-ones or pregn-14-en-20-ones. These synthetic methods are, however, not very economical and afford only cardenolides having a methyl group in position 10. In contrast, the present invention provides valuable 14-functionalized 19-oxygenated precursors to 19-oxygenated 14β-hydroxy cardenolides by novel and economical routes, in which the 19-oxygen atom assists in chemical transformations instead of encumbering them.

These precursors can readily be converted into the corresponding 14β-hydroxycardenolides by one or several of the well known methods. These methods together with the methods of this application allow the preparation of variously functionalized cardenolides, e.g. 19-oxygenated cardenolides; ;b 19-norcardenolides and unsaturated cardenolides. This functionalization makes it possible to bring about a medicinally desirable change in the kind and degree of cardiac activity. For example, studies on differently substituted cardenolides isolated from natural sources have shown that 19-oxygenated cardenolides are substantially more active than their 19-methyl-analogs, as described in Fieser and Fieser, Steroids, Chapter 20.

The conversion of the group R or R' in position 17 of the 14-functionalized 19-oxygenated precursors of this invention into the 17β-butenolide ring of the compounds of Formula XII and XIV may be carried out according to methods known to those skilled in the art, as for example summarized in Angewandte Chemie Vol. 9, No. 5, pp 321–332. Thus, for instance, 14β-hydroxy-14β-acetyl- as well as 14β-hydroxy-21-acetoxy-17β-acetyl steroids have been converted into 14β-hydroxy compounds having a butenolide ring in the 17β-position via initial transformation into the corresponding 20-ethoxyacetylen-20-ol and subsequent acid treatment which is, in the case of the 17β-acetyl steroids, followed by oxidation with selenium dioxide in boiling benzene, as described by F. Sondheimer, Chemistry in Britain, Vol. 1, No. 10, pp 454–464 (1965). While in the above method the butenolide side chain is introduced subsequent to the introduction of the 14β-hydroxy group, in other methods, as for example, described in Angewandte Chemie (supra), the 17β-butenolide side chain is introduced into compounds such as 14-dehydroanalogs not possessing a 14β-hydroxy group which is introduced in subsequent steps.

With regard to the other groups in the 17β-position, as specified above for general formula I, where the group R is CH₂Oacyl—CO it may be converted into the butenolide ring by the method described above for the transformation of a 21-acetoxy-17-acetyl steroid (R is CH₂OAc—CO). Where the group R is CH₂Oalkyl—CO it may be first converted to a group R where it is CH₂OH—CO by conventional methods. Subsequent acetylation affords then the above 21-acetate (R is CH₂OAc—CO) which then can be converted to the butenolide ring as described above. In the case where R is CH₂Oacyl—CH—Oacyl or CH₂Oalkyl—CH—Oalkyl conversion of these groups by conventional methods into group R where it is CH₂OH—CHOH followed by selective acetylation in position 21 and subsequent oxidation of the 20-hydroxy group by the method described, for example, in F. Sondheimer, Chemistry in Britain, cited above, affords then a group R which is $CH_2OAc-CO$, which may be converted to a butenolide ring according to the methods described above.

In the case where R is $CH_3-CH-Oacyl$, $CH_3-CH-Oalkyl$ or $CH_3-CH-OH$ conventional procedures, such as used for the generation of hydroxy groups from acylates and ethers respectively and subsequent oxidation, afford a 17β-acetyl group (where R is $CH_3-CO$), which may be converted to the butenolide ring by methods described above.

In the case where R is $CH_3CH-CHO$ the 17β-butenolide ring may be formed by conventional cyanohydrin formation followed by dehydration and conversion of the α,β-unsaturated nitrile obtained into the corresponding α,β-unsaturated 23-carboxylic acid ethyl ester, again by conventional methods, and subsequent treatment with selenium dioxide in boiling benzene as described by F. Sondheimer, Chemistry in Britain, cited above. In the case where R is $CH_3-CH-CH_2Oacyl$ or $CH_3-CH-CH_2Oalkyl$ conversion to the corresponding 22-alcohol, where R is $CH_3-CH-CH_2OH$ and oxidation to the above aldehyde, R being $CH_3-CH-CHO$, by conventional methods, may then afford the 17β-butenolide ring by the method described above. In the case where R is $CH_3-CH-CO_2H$, reduction of the carboxylic acid group to the above 22-aldehyde by conventional methods may then subsequently afford the 17-butenolide ring by the method described above.

In the case where R is $CH_3-CH-CH=CH-CH(CH_3)-CH(CH_3)_2$ or $CH_3-CH-CH=CH-(CH_2CH_3)-CH(CH_3)_2$ ozonolysis of the 20(22)-double bonds, as described, for example, by A. F. Daglish J. Chem. Soc., pp 2627–2633 (1954) affords then the above 22-aldehyde having R being $CH_3-CH-CHO$ which may then be converted to the butenolide ring by the method described above.

In the case where R is CN, conventional transformation to the corresponding methyl ester, R being $COOCH_3$, followed by conversion of the latter to a butenolide ring may be accomplished as described by F. Sondheimer, Chemistry in Britain, cited above. In the case where R is O= formation of the corresponding cyanohydrin, followed by conventional dehydration and hydrogenation, affords R being CN which can be converted to the 17β-butenolide ring as described above. In the case where R is OH, —Oacyl or —Oalkyl conversion of these groups into compounds where R is O= by conventional methods followed by application of the methods described above also yields the 17β-butenolide ring.

The starting materials used in processes (a) through (e) may be obtained according to the teachings of copending application Ser. No. 215,669.

It is an advantage of the processes (a) to (f) of the present invention that they allow the preparation of the 14-and 14,15-oxygenated 14-halogenated and 14-dehydro-8,19-oxides of formula I in good yield and without taking recourse to tedious and laborious purification techniques in contrast to previous preparations of 14,15-dehydro-8,19-oxides, which were obtained in low yield together with other steroidal products (see D. Hauser et al, vide supra).

It is a special advantage of processes (a) and (b) that they allow the preparation of 14β-hydroxy-8,19-oxides possessing 14β-hydroxy groups, which are one of the necessary structural features bringing about cardiotonic activities in steroids (vide supra, vide infra).

It is a special advantage of process (b) that it allows the preparation of 14β-hydroxy-8,19-oxides from 19-hydroxy-8β,14β-oxido steroids. The facile replacement of the ethereal 8β-oxygen atom by the β-situated 19-hydroxy group in the latter conversion by treatment under hydrogenation cannot be predicted by prior art teachings. According to the latter it would have been expected that chemical modifications brought about under these conditions are due to the hydrogenolysis of the oxirane ring (see, for example, R. L. Augustine, Catalytic Hydrogenation, Marcel Dekker, Inc., New York, 1965) in the 8β,14β-position rather than to intramolecular nucleophilic substitution.

As regards the preparation of the 14α-hydroxy-8,19-oxides of processes (a) and (b) respectively it is a special advantage that the intermediate 19-hydroxy-8α,14α-oxides either rearrange spontaneously or can be induced to rearrange completely to the latter oxides by mild acid treatment in the same reaction vessel in which they were formed, thus reducing, for practical purposes, the number of steps to these compounds.

With regard to process (a) it is of advantage that the 19-hydroxy-8β,14β-oxido-4,6-dien-3-ones and -3-ols of formula IIIa respectively rearrange to the corresponding 8,19-oxido-14β-ols under such mild conditions as treatment with acetic acid and without noticeable rearrangement reactions and formation of dehydration products as is the case, when saturated 8,14-oxido-19-methylsteroids are treated under acid conditions (see, for example, P. S. Janiak. E. Weiss, J. V. Euw and T. Reichstein, Helv., 46, 374 (1963); A. Lardon, T. Reichstein ibid, 46, 392 (1963); L. F. Fieser, M. Fieser, Steroids, Reinhold Publishing Corp., New York, 1959, p. 240). It is a particular advantage of the cyclisation of the 3,19-dihydroxy-8β,14β-oxido-4,6-dienes of formula IIIa by treatment with a weak acid that it takes place in a much more facile way than that of the 3-ketone analogs. Thus the formation of 3,14β-dihydroxy-8,19-oxido-4,5-dienes from the corresponding 19-hydroxy-8β,14β-oxido-4,6-dien-3-ones of formula IIIa, and their rearrangement to the 8,19-oxido-4,6-dien-3-ols can be brought about conveniently in the same reaction vessel at the same temperature by successive treatment with a metal hydride and an acid, i.e. without isolation of the intermediate 3,19-dihydroxy-8β,14β-oxido-4,6-diene.

It is a special advantage of processes (e) and (f) that the oxidative cyclisation of the 19-alcohols used as starting materials can be brought about under mild reaction conditions, e.g. at room temperature and below, and that the oxidative cyclisation proceeds in a highly selective manner. This is in contrast to previously reported oxidative cyclisations of 19-hydroxy steroids, which require heating, and activation by light and yield a multiplicity of products (see D. Hauser vide supra). There appear to be no reports in the literature that oxidative cyclisations of the above type can be brought about by such mild oxidizing reagents as manganese dioxide.

It is an unexpected feature of the oxidative cyclisation brought about by manganese dioxide that it proceeds in a particularly facile manner, when 19-hydroxy-8(14)-enes possessing a 4,6-dien-3-one moiety are used as starting materials. This is of particular advantage as oxidative or dehydrative methods, by which 8,19-oxido-14-enes with saturated A- an B-rings can readily be prepared from the corresponding 19-hydroxy-8(14)-enes or 8,19-oxido-14-ols, respectively, fail or proceed with extensive by-product formation when the 4,6-dien-3-one moeity is present in the latter starting materials.

It is an advantage of process (g) that the 8α,14α-oxide XVI can be prepared in high yield and without concomitant formation of the isomeric 8β, 14β-oxide, which is difficult to separate from the isomeric major product because of the similarity in physical properties of the two isomers. It is a special advantage of process (g) that the 19-hydroxy group need not be regenerated from the 19-alkyl ethers prior to treatment under hydrogenation conditions, so that the latter treatment affords the 14α-hydroxy-8,19-oxides of Formula I in a single step from the 19-alkyl ethers of Formula XVI. It is an unexpected feature, and a further advantage, of process (g) that in the case where alkyl in Formula XVI is tetrahydropyranyl, cyclisation to the 14α-hydroxy-8,19-oxide (1) can readily be brought about by hydrogenation conditions at room temperature using acetic acid as a solvent and palladium as a catalyst, since the 19-tetrahydropyranyl group cannot normally be removed under such mild conditions; e.g. when 19-tetrahydropyranyl ether XVI is subjected to the above conditions no reaction takes place and the 19-hydroxy groups is only regenerated from the tetrapyranyl ether when the compound is heated in aqueous acetic acid for prolonged periods of time. Apparently the fission of the 19-oxygen tetrahydropyranyl bond is facilitated by the incipient bond formation of the 19-oxygen atom with the electrophilic 8-carbon atom of the 8α,14α-oxide so that the transformation of tetrahydropyranyl ether XVI to the corresponding 14α-hydroxy-8,19-oxide (I) takes place by a concerted process without formation of the corresponding 19-alcohol as an intermediate.

It is a special advantage of process (h) that in the special epoxidation procedure employed the conversion of the 3-oxo-4,6,8(14)-trien-19-al to the corresponding 3-oxo-8α,14α-oxido-4,6-dien-19-al can be accomplished with a high degree of selectivity, so that the double bonds in position 4 and 6 remain largely unaffected and essentially only the 8α,14α-oxide is obtained. It is a further advantage of the special epoxidation conditions that the labile 8α,14α-oxido-19-aldehyde remains intact until all starting material has been consumed, since when the usual epoxidation conditions were employed (see for example L. F. Fieser and M. Fieser, Reagents for Organic Synthesis, John Wiley and Sons, New York, 1967, pp 136 and 137), the reaction product contained only little of the desired 8α,14α-oxido-4,6-dien-19-al besides numerous by-products. It is a further advantage of process (h) that the reduction of the intermediate 8α,14α-oxido-19-ol XVIII yields the 8,19-oxido-14α-ol (1) in a single step rather than proceeding via an intermediate 19-hydroxy analog requiring special conditions for the cyclisation to the 14α-hydroxy-8,19-oxide (1).

As regards the formation of 14-acetates from the corresponding 14-alcohols under acidic conditions there seem to be no disclosures in the literature of such conversions, it being generally held that 14-hydroxy steroids, when treated with acids, alone or in presence of esterifying agent, yield the corresponding 14,15- or 8(14)-enes. The above derivitization of 14-hydroxy steroids is of special value in the synthesis of cardiotonic cardenolides since the free 14-hydroxy groups interact readily with the 17β-butenolide ring and according to F. Sondheimer, Chemistry in Britain, 1, 454 (1965) "no method of the protection of the 14β-hydroxy group is known" so far.

Having thus generally described the invention, reference will now be made to the accompanying Examples illustrating preferred embodiments.

EXAMPLE 1

A mixture of 200 mg of 3β,19-dihydroxy-8β,14β-oxido-17β-pivaloxy-5α-androstane, 100 mg of 5% paladium on charcoal and 20 ml of acetic acid was shaken in an atmosphere of hydrogen for 3 hours whereupon it was diluted with toluene and filtered through celite and cotton wool. The filtrate was evaporated at reduced pressure to yield a white foam consisting mainly of 3β,14β-dihydroxy-8,19-oxido-17β-pivaloxy-5α-androstane. A mixture of the white foam, 0.8 ml of pyridine and 0.4 ml of acetic anhydride was then left to stand under nitrogen for 16 hours at room temperature whereupon 12 ml of water was added. Extraction of the mixture with 2 volumes of ether followed by 3 washings of the ethereal phase with water and evaporation at reduced pressure gave a residue which crystallized on treatment with n-hexane yielding, after decantation of the supernatant liquid, 3β-acetoxy-14β-hydroxy-8,19-oxido-17β-pivaloxy-5α-androstane, mp 133°–135° C., the structure of which was verified by elemental analysis, mass spectroscopy and ir spectroscopy.

EXAMPLE 2

A mixture of 2.7 g of 3β,19-dihydroxy-17β-pivaloxy-5α-androst-8(14)-ene, 2,700 ml of carbon tetrachloride and 2.1 g of metachloroperbenzoic acid was left to stand for 4.5 hours at room temperature whereupon it was extracted 3 times with 200 ml of 2% aqueous potassium hydroxide and once with 120 ml of water. Drying with sodium sulfate, evaporation at reduced pressure, treatment of the gelatinous residue obtained with hexane and filtration gave 2.57 g of a white solid consisting mainly of 3β,19-dihydroxy-8β,14β-oxido-17β-pivaloxy-5α-androstane and a smaller amount of 3β, 14α-dihydroxy-8,19-oxido-17β-pivaloxy-5α-androstane. A mixture of 500 mg of the latter two compounds, 50 ml of acetic acid and 250 mg of 5% palladium on charcoal was stirred magnetically in an atmosphere of hydrogen for one hour at room temperature whereupon the hydrogen atmosphere was replaced by nitrogen, and 200 ml of ether was added. The mixture was then filtered through cotton wool and celite, cooled in an ice bath and treated with 100 ml of 50% aqueous potassium hydroxide and 150 ml of water. The alkaline phase was separated, the ethereal phase was washed with water to neutrality and then dried with sodium sulfate. Evaporation at reduced pressure gave a resinous material which was chromatographed on thick layer plates coated with silica gel G. Elution with ethyl acetate-benzene 1:1 gave 3 fractions consisting of 3β,14β-dihydroxy-8,19-oxido-17β-pivaloxy-5α-androstane, 3β,14β,19-trihydroxy-17β-pivaloxy-5α-androst-7-ene and 3β,14α-dihydroxy-8,19-oxido-17β-pivaloxy-5α-androstane, respectively. Treatment of these compounds with an excess of acetic anhydride-pyridine 1:2 at room temperature under nitrogen for 16 hours followed by addition of 20 volumes of ether, 5 volumes of water, extraction of the ethereal phase with water and evaporation at reduced pressure afforded the corresponding mono- and diacetates, namely, 3β-acetoxy-14β-hydroxy-8,19-oxido-17β-pivaloxy-5α-androstane, as evidenced by comparison of its ir spectrum with that of the product obtained in Example 1; 3β,19-diacetoxy-14β-hydroxy-17β- pivaloxy-5α-androst-7-ene, as evidenced by comparison with an authentic product (see patent application Ser. No. 215,669), and 3β-acetoxy-14α-hydroxy-8,19-oxido-17β-pivaloxy-5α-androstane, mp 207°–208° C., ir (KBr) 3515, 1726, 1710, 1240 and 1180 cm$^{-1}$.

EXAMPLE 3

A mixture of 20 mg of 3β-acetoxy-14α-hydroxy-8,19-oxido-17β-pivaloxy-5α-androstane, 1 ml of pyridine and 0.02 ml of thionyl chloride was left to stand for 55 minutes at room temperature whereupon it was cooled by an ice bath and 1.5 ml of water was added. The mixture was left to stand in the ice bath for 1 hour whereupon 9.0 ml of additional water was added. Filtration of the resulting precipitate gave 3β-acetoxy-8,19-oxido-17β-pivaloxy-5α-androst-14-ene, mp 192.5° to 193° C., as verified by ir and mass spectroscopy.

EXAMPLE 4

A mixture of 70 mg of 3β-acetoxy-14β-hydroxy-8,19-oxido-17β-pivaloxy-5α-androstane, 3.5 ml of pyridine and 0.07 ml of thionyl chloride was left to stand for 55 minutes at room temperature whereupon it was cooled in an ice bath and 5.0 ml of water was added. After 1 hour standing in the ice bath, 30 ml of water was added and the mixture was filtered, yielding 43 mg of a precipitate which was dissolved in ether. A small amount of petroleum ether was added, followed by charcoal and the mixture was filtered through celite. Concentration of the filtrate and addition of petroleum ether gave 3β-acetoxy-8,19-oxido-17β-pivaloxy-5α-androst-14-ene mp 190°–192° C., as verified by comparison of its ir spectrum with that of the product obtained in Example 3.

EXAMPLE 5

A mixture of 25 mg of 19-hydroxy-8β,14β-oxido-17β-pivaloxy-androsta-4,6-dien-3-one and 0.25 ml of acetic acid was heated in an atmosphere of nitrogen at 75° C. for 60 mins. Evaporation at reduced pressure gave 14β-hydroxy-8,19-oxido-17β-pivaloxyandrosta-4,6-dien-3-one, ir (KBr) 3400, 1720 1675 1655 (sh), 1610, 1580, 1170, 1155 (sh) and 987 cm$^{-1}$.

EXAMPLE 6

To a mixture of 30 mg of 14β-hydroxy-8,19-oxido-17β-pivaloxyandrosta-4,6-dien-3-one and 0.3 ml of methanol, which was cooled externally by an ice bath, was added 6 mg of sodium borohydride with stirring. Stirring was continued for 5 minutes whereupon 6 ml of water was added. The mixture was extracted with ether, the ethereal phase was extracted with water and then evaporated to yield 3β,14β-dihydroxy-8,19-oxido-17β-pivaloxyandrosta-4,6-diene, uv max 244 mμ, which was further verified by tlc analysis.

EXAMPLE 7

A mixture of 6 mg of 3β,19-dihydroxy-8β,14β-oxido-17β-pivaloxyandrosta-4,6-diene and 0.12 ml of acetic acid was left to stand at room temperature for 70 minutes, whereupon an excess of potassium hydroxide-water 1:10 was added. Filtration yielded a white precipitate of 3β,14β-dihydroxy-8,19-oxido-17β-pivaloxyandrosta-4,6-diene, uv max 244 mμ and as verified by ir and mass spectroscopy.

EXAMPLE 8

A mixture of 200 mg of 19-hydroxy-17β-pivaloxy-androsta-4,6,8(14)-trien-3-one, 4.0 ml of methanol-water 95:5 and 1.712 ml of a solution, prepared from 37.8 ml of 0.5 molar perbenzoic acid in methylene chloride and 8.9 ml of methanol water 95:5, was left to stand for 2 days at 35° C. whereupon 40 ml of ether was added. The mixture was then extracted several times with 2% aqueous potassium hydroxide, dried with sodium sulfate and evaporated at reduced pressure. A mixture of the residue obtained, 0.8 ml of pyridine and 0.4 ml of acetic anhydride was then left to stand at 35° C. for 16 hours. Subsequent addition of water and extraction with ether followed by extraction of the ethereal phase with water and evaporation at reduced pressure gave an oil which was treated with petroleum ether. The resulting solid was collected by filtration and dissolved in methylene chloride. A small amount of petroleum ether was added followed by charcoal. Filtration through diatomaceous earth followed by addition of petroleum ether to the filtrate, concentration at reduced pressure and filtration gave 14α-hydroxy-8,19-oxido-17β-pivaloxyandrosta-4,6-dien-3-one, mp 218°–220° C., as verified by ir, nmr and mass spectroscopy.

The latter compound could also be obtained in a very similar manner when instead of perbenzoic acid, meta-chloroperbenzoic acid was used and the epoxidation was carried out in tertiary butanol or in methylene chloride.

EXAMPLE 9

A mixture of 70 mg of 14α-hydroxy-8,19-oxido-17β-pivaloxyandrosta-4,6-dien-3-one, 3.5 ml of isopropenyl acetate and 70 mg of paratoluenesulfonic acid was heated at 105° C. under N$_2$ for 30 minutes whereupon it was cooled, extracted seven times with water, dried with sodium sulfate and evaporated at reduced pressure. Treatment of the residue obtained with methanol gave 22.9 mg of pale yellow crystals of 3,14α-diacetoxy-8,19-oxido-17β-pivaloxyandrosta-2,4,6-triene, uv max 302 mμ, ir (KBr) 1760, 1730, 1365, 1280, 1240, 1225, 1217, 1205, 1190 and 1155 cm$^{-1}$.

EXAMPLE 10

A mixture of 20.0 mg of 3,14α-diacetoxy-8,19-oxido-17β-pivaloxyandrosta-2,4,6-triene and 1.0 ml of 0.2 N methanolic potassium hydroxide was left to stand at room temperature under nitrogen for 1 hour whereupon 1.1 ml of a 0.2 N solution of acetic acid in ethyl acetate was added. The solvent was then evaporated at reduced pressure, the residue obtained was treated with ethyl acetate and the mixture was filtered. Evaporation of the filtrate at reduced pressure gave a residue which was digested with petroleum ether-ether 9:1 to yield, after filtration, 5.9 mg of 14α-acetoxy-8,19-oxido-17β-pivaloxyandrosta-4,6-dien-3-one as a white precipitate, mp 153°–154° C., uv max 289 mμ and as verified by ir and mass spectroscopy.

EXAMPLE 11

A mixture of 20 mg of 14α-hydroxy-8,19-oxido-17β-pivaloxyandrosta-4,6-dien-3-one and 0.2 ml of methanol was cooled externally by an ice-bath whereupon 5 mg of sodium borohydride was added. The mixture was agitated for 5 minutes and 2.0 ml of water was added. Extraction with 4.0 ml of ether, followed by 4 extractions of the ethereal phase with 1.0 ml of water and evaporation gave 3β,14α-dihydroxy-8,19-oxido-17β-pivaloxyandrosta-4,6-diene, uv max 244 mμ. A mixture of the latter material, 0.02 ml of acetic anhydride and 0.04 ml of pyridine was left to stand at room temperature for 16 hours, whereupon 0.02 ml of water was added followed by, after 1 hour of standing, 0.20 ml of additional water. Filtration of the resulting precipitate gave 14.6 mg of 3β-acetoxy-14α-hydroxy-8,19-oxido-17β-pivaloxyandrosta-4,6-diene, ir(KBr) 3520, 3500, 1725 and 1245 cm$^{-1}$.

EXAMPLE 12

A solution of 160 mg of 3-oxo-17β-pivaloxyandrost-4,6,8(14)-trien-19-al and 120 mg of meta chloroperbenzoic acid in 160 ml of carbon tetrachloride was left to stand at room temperature for 16 hours whereupon it was extracted three times with 2% aqueous potassium hydroxide, dried with sodium sulfate and evaporated. Several recrystallizations of the residue obtained from ether-petroleum ether gave 37.9 mg of pale yellow crystals of 3-oxo-8α,14α-oxido-17β-pivaloxyandrosta-4,6-dien-19-al, mp 127°–129° C., ir (KBr) 1730, 1725, 1670, 1620, 1590 and 1160 cm$^{-1}$.

EXAMPLE 13

An agitated mixture of 20 mg of 3-oxo-8α,14α-oxido-17β-pivaloxyandrosta-4,6-dien-19-al, and 0.2 ml of methanol was cooled externally by an ice-bath whereupon 10 mg of sodium borohydride was added. The mixture was agitated further for 15 minutes and 2.0 ml of water was added. Extraction with 4 ml of ether, followed by extraction of the ethereal phase with 4 × 1 ml of water and evaporation at reduced pressure gave a product, uv max 246 mμ, consisting essentially of 3β,14α-dihydroxy-8,19-oxido-17β-pivaloxyandrosta-4,6-diene, as evidenced by the comparison with the intermediate product obtained as described in Example 11. A mixture of the crude product, 0.020 ml of acetic anhydride and 0.040 ml of pyridine was left to stand at room temperature for 16 hours whereupon it was diluted with water. Extraction with ether followed by extraction of the ethereal phase with water, evaporation at reduced pressure, chromatography on silica gel G coated glass plates followed by elution with ethyl acetate benzene 1:4 gave 3β-acetoxy-14α-hydroxy-8,19-oxido-17β-pivaloxyandrosta-4,6-diene as evidenced by the identity of its ir spectrum and that of its tlc chromatogram with those of the product obtained in Example 11.

EXAMPLE 14

A mixture of 300 mg of 19-acetoxy-8β,14β-oxido-17β-pivaloxyandrosta-4,6-dien-3-one and 6.0 ml of methanol was cooled externally by an ice-bath below 5° C. whereupon 30 mg of sodium borohydride was added in small portions with agitation. A small sample was withdrawn 5 minutes after addition of the latter reagent and added to an ether-water mixture. The ether solution had uv max 245 mμ indicating the presence of 19-acetoxy-3β-hydroxy-8β,14β-oxido-17β-pivaloxyandrosta-4,6-diene, as also verified by tlc-analysis. Fifteen minutes after the addition of the sodium borohydride a solution 0.6 ml of 2 N methanolic potassium hydroxide was added and the mixture was left to stand at room temperature under nitrogen for 3.5 hours, whereafter 0.3 ml of glacial acetic acid was added. Tlc analysis of the mixture indicated the presence of 3β,19-dihydroxy-8β,14β-oxido-17β-pivaloxyandrosta-4,6-diene as the major steroidal product in the reaction mixture. One hour after the addition of the glacial acetic acid 1.0 ml of a further lot of the latter was added. Tlc-analysis on the reaction mixture after 20 minutes indicated the presence of 3β,14β-dihydroxy-8,19-oxido-17β-pivaloxyandrosta-4,6-diene. Forty minutes after addition of the second lot of glacial acetic acid 60 mg of 5% of palladium on charcoal was added and the mixture was shaken under hydrogen for 2 hours, whereupon 60 ml of ether was added and the mixture was filtered through celite. Extraction with 10% aqueous potassium hydroxide and water, followed by drying with sodium sulphate and evaporation gave a resin which was treated with hexane. The hexane extracts were evaporated and chromotographed on a thick layer plate coated with silica gel G. Elution with ethyl acetate-benzene 1:1 afforded as the major fraction 28.1 mg of 3β,14β-dihydroxy-8,19-oxido-17β-pivaloxy-5α-androstane. A mixture of the latter product and approximately 0.5 ml of pyridine-acetic anhydride 2:1 was left to stand at room temperature under nitrogen for 16 hours, whereafter 10 volumes of water were added. The mixture was left to stand for 2 hours and was then filtered to yield 3β-acetoxy-14β-hydroxy-8,19-oxido-17β-pivaloxy-5α-androstane, as evidenced by comparison of the ir-spectrum of the product obtained with that of the product obtained in Example 1.

EXAMPLE 15

A mixture of 175 mg of 14α-hydroxy-8,19-oxide-17β-pivaloxyandrosta-4,6-diene-3-one and 8.75 ml of methanol was cooled externally by an ice bath below 10° C. whereupon 17.5 mg of sodium borohydride was added with agitation. The mixture was agitated for 15 minutes and another lot of 17.5 mg of sodium borohydride was added. After 45 minutes, uv analysis revealed only a peak at 240 mμ, indicating that all starting material had been converted to 3β,14α-dihydroxy-8,19-oxido-17β-pivaloxyandrosta-4,6-diene. To the above reaction mixture was then added a suspension of 35 mg of 5% palladium on charcoal in 2.1 ml of methanol. The total mixture was agitated in an atmosphere of hydrogen for 16 hours at room temperature whereupon approximately 20 volumes of ether were added. The mixture was filtered through celite and the filtrate was evaporated at reduced pressure to give a residue which crystallized on treatment with hexane yielding 90 mg of 3β,14α-dihydroxy-8,19-oxido-17β-pivaloxy-5α-androstane as a white solid. A mixture of the latter, 0.6 ml of pyridine and 0.3 ml of acetic anhydride was left to stand under nitrogen at room temperature for 16 hours whereupon 10 volumes of water were added. The mixture was left to stand for a further 2 hours and then filtered. The precipitate was recrystallized from methanol and then from pentane, yielding 38 mg of 3β-acetoxy-14α-hydroxy-8,19-oxido-17β-pivaloxy-5α-androstane, as verified by comparison of the ir spectrum of the product obtained with that of the ir spectrum of the product obtained according to Example 2.

EXAMPLE 16

A mixture of 600 mg of 3β,17β,19-trihydroxy-5α-androst-8(14)-ene, 12 ml of pyridine and 720 mg of pyridinium hydrobromide perbromide was shaken under nitrogen for 4 hours. TLc analysis of a sample of the mixture indicated that the latter then contained 3β,17β-dihydroxy-8,19-oxido-5α-androst-14-ene as the major steroidal product. 2.4 ml of acetic anhydride was added to the mixture which was shaken under nitrogen for a further 19 hours, whereafter 2 volumes of water were added. After 5 further minutes 16 volumes of water was further added, and shaking was continued for 30 minutes. The mixture was then filtered yielding 627 mg of 3β,17β-diacetoxy-8,19-oxido-5α-androst-14-ene as verified by tlc analysis and by ir spectroscopy as well as by the conversion of the product into 3β,17β-diacetoxy-19-hydroxy-14α,15α-oxido-5α-androstane described in pending patent application Ser. No. 718,921 filed Aug. 30, 1976.

EXAMPLE 17

A mixture of 5 mg of 3β,19-dihydroxy-17β-pivaloxy-5α-androst-8(14)-ene, 0.1 ml of pyridine and 5 mg of pyridinium hydrobromide perbromide was stirred under nitrogen for 105 minutes, whereupon it was divided into 2 equal halves. To one half of the mixture, 0.02 ml of acetic anhydride was added. After 16 hours of standing in the nitrogen at room temperature, 10 volumes of water were added and the mixture was extracted with ether. The ethereal phase was extracted four times with water and evaporated. The residue obtained was treated with ether petroleum ether yielding 3β-acetoxy-8,19-oxido-17β-pivaloxy-5α-androst-14-ene as a crystalline material, ir (KBr) 2930, 2845, 1726, 1240, 1170, and 1155 cm$^{-1}$. The other half of the mixture was left to stand for another 18 hours whereupon water was added. Filtration gave a material consisting essentially of 3β-hydroxy-8,19-oxido-17β-pivaloxy-5α-androst-14-ene as indicated by tlc analysis. A mixture of the latter material, 8 drops of pyridine and 4 drops of acetic anhydride was then left to stand under nitrogen at room temperature for 16 hours whereupon 10 volumes of water were added. The mixture was extracted with ether, the ethereal phase was washed several times with water and evaporated at reduced pressure yielding a solid consisting of 3β-acetoxy-8,19-oxido-17β-pivaloxy-5α-androst-14-ene; ir (KBr) 2925, 2850, 1726, 1240, 1170 and 1155 (sh) cm$^{-1}$.

EXAMPLE 18

A mixture of 10 mg of 3β,19-dihydroxy-17β-pivaloxy-5α-androst-8(14)-ene, 2 ml of ether and 160 mg and activated manganese dioxide was agitated at room temperature for 2.5 hours. Tlc analysis showed that 3β-hydroxy-8,19-oxido-17β-pivaloxy-5α-androst-14-ene was the major steroidal material in the mixture besides some starting material.

EXAMPLE 19

A mixture of 5 mg of 3β,19-dihydroxy-17β-pivaloxy-5α-androst-8(14)-ene, 8.5 mg of lead tetraacetate, 0.19 ml of benzene and 0.36 ml of methanol-borontrifluoride etherate 1.8:5.04 was agitated in the absence of light at room temperature for 2.5 hours whereupon it was diluted with ether, extracted with water to neutrality, filtered through celite and evaporated. Tlc anlysis of the product and its acetate, which was prepared by a treatment with pyridine and acetic anhydride as described in example 17, indicated that 3β-hydroxy-8,19-oxido-17β-pivaloxy-5α-androst-14-ene was the major reaction product.

EXAMPLE 20

A mixture of 3 mg of 3β,19-dihydroxy-17β-pivaloxy-5α-androst-8(14)-ene, 7.5 mg of lead tetraacetate and 0.3 ml of carbon tetrachloride was heated at 70° C. for 1 hour whereupon it was diluted with 5 volumes of ether and extracted with aqueous sodium thiosulphate. Evaporation of the ethereal phase at reduced pressure gave a white solid product consisting of 3β-hydroxy-8,19-oxido-17β-pivaloxy-5α-androst-14-ene as practically the only steroidal product as evidenced by tlc analysis.

EXAMPLE 21

An ethereal solution of 3β,19-dihydroxy-17β-pivaloxy-5α-androst-8(14)-ene was treated with small lots of bromine until addition of a small amount of the latter lead to a persistent yellow colour. Evaporation at reduced pressure gave a product consisting mainly of 14-bromo-3β-hydroxy-8,19-oxido-17β-pivaloxy-5α-androstane as evidenced by tlc analysis and by the chemical conversion described in Example 22.

EXAMPLE 22

A mixture of the product obtained as described in Example 21 and pyridine acetic anhydride 2:1 was left to stand at room temperature under nitrogen overnight. Immediately after addition of the pyridine acetic anhydride, a brown colour developed. Working up by dilution with water and extraction with ether as described in Example 17 gave a product consisting mainly of 3β-acetoxy-8,19-oxido-17β-pivaloxy-5α-androst-14-ene as evidenced by tlc analysis.

EXAMPLE 23

A mixture of 1g of 3β,19-dihydroxy-20β-pivaloxy-5α-pregn-8(14)-ene, 20 ml of pyridine and 763 mg of pyridinium hydrobromide perbromide was stirred at room temperature under nitrogen and in the dark for 4 hours whereupon 200 ml of 0.5% aqueous sodium bisulfate followed by 70 ml of concentrated hydrochloric acid-water 1:3 and 50 ml of pentane was added. The mixture was stirred for 30 minutes and the initially gelatinous precipitate was collected by filtration, yielding after drying at high vacuum at 45° C., 769 mg of 3β-hydroxy-8,19-oxido-20β-pivaloxy-5α-pregn-14-ene, mp 142°–143° C. (sagging at 134° C.) as verified by tlc analysis, conversion to the corresponding 3-acetate and ir spectroscopy.

EXAMPLE 24

A mixture of 50 mg of 3β,19-dihydroxy-20β-pivaloxy-5α-pregn-8(14)-ene, 0.09 ml of methanol, 1.9 ml of benzene, and 85 mg of lead tetraacetate was stirred for 2 hours at room temperature whereupon the brown mixture was diluted with ethyl acetate and extracted with 0.1 N sodium thiosulphate which brought about discolouration of the mixture. Evaporation of the organic phase followed by addition of hexane, gave 23 mg of 3β-hydroxy-8,19-oxido-20β-pivaloxy-5α-pregn-14-ene as verified by tlc analysis and ir spectroscopy.

EXAMPLE 25

A mixture of 50 mg of 3β-hydroxy-8,19-oxido-20β-pivaloxy-5α-pregn-14-ene, 0.3 ml of benzene, 0.2 ml of benzenedihydropyrane, 3.4:1.6 and 0.5 ml of benzene phosphorus oxychloride 100:1 was stirred at room temperature under nitrogen for 3 hours, whereupon 1 ml of 4% aqueous-sodium bicarbonate was added, followed by 1 volume of benzene. The organic phase was extracted with water and evaporated to yield white solid consisting of 8,19-oxido-20β-pivaloxy-5α-pregn-14-en-3β-yl 2'-tetrahydropyranyl ether, as indicated by tlc analysis, which was used for the next reaction.

EXAMPLE 26

A mixture of the product obtained as described in the preceding example and 1 ml of an approximately 11.7% solution of sodium bis(2-methoxyethoxy)aluminum hydride in benzene was stirred under nitrogen at room temperature for 45 minutes whereupon 0.1 ml of a 1% aqueous sodium bicarbonate solution was added gradually with stirring. The mixture was then evaporated at reduced pressure in the presence of ethylacetate. The ethy acetate solution obtained was dried with sodium sulfate and filtered through diatomaceous earth. Evaporation gave a semi-solid consisting essentially of 20$\beta$-hydroxy-8,19-oxido-5$\alpha$-pregn-14-en-3$\beta$-yl 2'-tetrahydropyranyl ether, as indicated by tlc analysis, which was used in the reaction described in the following example.

EXAMPLE 27

A mixture of the product obtained as described in the preceding example and 1.25 ml of pyridine was cooled externally by an ice bath in an atmosphere of nitrogen whereupon 70 mg of chromium trioxide was added over a period of 2 minutes. The mixture was stirred at 0° C. for approximately 1 hour and then at room temperature for 6 hours whereafter 0.7 ml of isopropanol was added, followed by, after 30 minutes of stirring, 3 volumes of methylene chloride. The mixture was then filtered through approximately 10 parts of aluminium oxide, the filtrate was evaporated at reduced pressure in the presence of toluene and benzene. The benzene solution, finally obtained, was treated with charcoal and then filtered through diatomaceous earth. Evaporation of the filtrate gave a residue which was digested with pentane to yield 20-oxo-8,19-oxido-5$\alpha$-pregn-14-en-3$\beta$-yl 2'-tetrahydropyranyl ether, ir (KBr) 2930, 2850, 1700, 1365, 1120 and 1030 cm$^{-1}$.

EXAMPLE 28

To a mixture of 51 mg of lead tetraacetate and 0.57 ml of benzene was added a solution of 10 mg of 20-oxo-8,19-oxido-5$\alpha$-pregn-14-en-3$\beta$-yl 2'-tetrahydropyranyl ether in 0.57 ml of benzene followed by a solution of 0.054 ml of methanol in 0.168 ml of boron trifluoride-etherate. The mixture was protected from light and stirred at room temperature for 4.5 hours, whereafter the precipitate, which had formed, was removed by filtration. The filtrate was diluted with 1 volume of ethyl acetate and then extracted several times with half a volume of water. Evaporation at reduced pressure gave a resinous material consisting essentially of 21-acetoxy-3$\beta$-hydroxy-8,19-oxido-5$\alpha$-pregn-14-en-20-one as indicated by tlc analysis. A mixture of the latter material and an excess of pyridine acetic anhydride 2:1 was left to stand at room temperature under nitrogen for 18 hours, whereupon it was evaporated at high vacuum. The residue obtained was dissolved in ether and extracted several times with water. Evaporation of the ethereal phase gave a residue which on treatment with methanol, followed by evaporation and treatment with ether-hexane 1:1 gave a white solid consisting of 3$\beta$,21-diacetoxy-8,19-oxido-5$\alpha$-pregn-14-en-20-one ir (KBr) 2930, 2890, 2850, 1750, 1730, 1725 (sh), 1255 and 1235 cm$^{-1}$.

EXAMPLE 29

A mixture of 1 mg of 3$\beta$-acetoxy-8,19-oxido-17$\beta$-pivaloxy-5$\alpha$-androst-14-ene, 1 mg of meta chloroperbenzoic acid and 1 ml of carbon tetrachloride was left to stand at room temperature for 5 hours whereupon it was extracted 3 times with 2% aqueous potassium hydroxide and then with water. Evaporation at reduced pressure gave 3$\beta$-acetoxy-8,19; 14,15-dioxido-17$\beta$-pivaloxy-5$\alpha$-androstane as evidenced by tlc analysis.

EXAMPLE 30

A mixture of 168 mg of 3$\beta$-acetoxy-8,19-oxido-20$\beta$-pivaloxy-5$\alpha$-pregn-14ene, 160 ml of carbon tetrachloride and 153 mg of meta chloroperbenzoic acid was left to stand under nitrogen at room temperature for 2.5 hours and then at −5° C. for 18 hours. Extraction with 3 lots of 36 ml of 2% aqueous potassium hydroxide followed by 2 extractions with 36 ml of water and evaporation, gave a product which was purified by thick layer chromatograph on silica gel G. Elution with ethyl acetate-benzene 1:10 gave 3$\beta$-acetoxy-8,19; 14,15-dioxido-17$\beta$-pivaloxy-5$\alpha$-pregnane as evidenced by tlc analysis.

EXAMPLE 31

To a mixture of 200 mg of 19-hydroxy-17$\beta$-pivaloxyandrosta-4,6,8(14)-trien-3-one, and 40 ml of ether was added 400 mg of activated manganese dioxide. The mixture was shaken for 22 hours during which time 5 further lots, each amounting to 800 mg, of manganese dioxide were added. Filtration through diatomaceous earth followed by evaporation at reduced pressure and recrystallization of the residue obtained from ether gave 55.1 mg of 8,19-oxido-17$\beta$-pivaloxyandrosta-4,6,14-trien-3-one, ir (KBr) 3075, 2955, 2865, 1730, 1655, 1285 and 1175 cm$^{-1}$.

EXAMPLE 32

To a mixture of 200 mg of 19-hydroxy-20$\beta$-pivaloxy pregn-4,6,8(14)-trien-3-one and 40 ml of ether was added 200 mg of activated manganese dioxide. The mixture was shaken for 28 hours at room temperature during which time another lot of 200 mg and 3 further lots of 800 mg each of manganese dioxide were added. The mixture was then filtered through diatomaceous earth and 1 volume of hexane was added to the filtrate. Concentration at reduced pressure followed by filtration gave 85 mg of 8,19-oxido-20$\beta$-pivaloxy pregn-4,6,14-trien-3-one, mp 207°–207.5° C. The structure of the compound obtained was verified by ir and nmr spectroscopy.

EXAMPLE 33

A mixture of 2 mg 3$\beta$,19-dihydroxy-20$\beta$-pivaloxy pregn-4,6,8(14)-triene and 0.5 ml of ether was treated with manganese dioxide under reaction conditions which were essentially the same as the one described in the preceding example. After working up a mixture of 8,19-oxido-20$\beta$-pivaloxypregn-4,6,14-trien-3-one and 19-hydroxy-20$\beta$-pivaloxypregn-4,6,8(14)-trien-3-one was obtained as indicated by tlc analysis.

EXAMPLE 34

A mixture of 3 mg of 19-hydroxy-20$\beta$-pivaloxypregn-4,6,8(14)-trien-3-one, 7.5 mg of lead tetraacetate and 0.3 ml of carbon tetrachloride was agitated for 19 hours whereupon it was extracted with aqueous sodium thiosulfate and evaporated at reduced pressure to yield a mixture of the starting material and 8,19-oxido-20β-pivaloxypregn-4,6,14-trien-3-one as indicated by tlc analysis.

EXAMPLE 35

A mixture of 47.5 mg of 8,19-oxido-20β-pivaloxypregn-4,6,14-trien-3-one, 4.75 ml of tert. butylamine and 5 mg of 5% palladium on charcoal was agitated in an atmosphere of hydrogen at room temperature for 3 hours whereupon 3 volumes of ethyl acetate were added, and the mixture was filtered through diatomaceous earth under nitrogen. The filtrate was evaporated under reduced pressure, the residue obtained was treated with ether and filtered. Addition of hexane to the filtrate followed by filtration gave 36.6 mg of 8,19-oxido-20β-pivaloxy-pregna-4,14-dien-3-one, uv max 242 mµ.

EXAMPLE 36

A mixture of approximately 10 mg of 8,19-oxido-20β-pivaloxypregn-4,14-dien-3-one, 1 ml of tert. butylamine and 5 mg of 5% of palladium on charcoal was shaken at room temperature in an atmosphere of hydrogen for 2.5 hours, whereupon it was diluted with ethyl acetate and filtered through diatomaceous earth under nitrogen. Evaporation at reduced pressure gave a product uv max 210 mµ consisting of 8,19-oxido-20β-pivaloxy-5β-pregn-14-en-3-one, and the corresponding 5α isomer, as evidenced by tlc analysis.

EXAMPLE 37

A mixture of 50 mg of 19-hydroxy-20β-pivaloxy-4,6,8(14)-trien-3-one, 50 ml of carbon tetrachloride, and 40 mg of meta chloroperbenzoic acid was left to stand under nitrogen at room temperature in the dark for 1 day whereupon it was extracted three times with 20 ml of 2% aqueous potassium hydroxide and once with 40 ml of water. The mixture was then filtered to remove undissolved starting material and the filtrate was concentrated at reduced pressure. Addition of ether-hexane followed by concentration at reduced pressure and filtration gave a white precipitate of 19-hydroxy-8β,14β-oxido-17β-pivaloxy-pregna-4,6-dien-3-one, uv max 287 mµ; tlc analysis indicated that besides the latter product, a small amount of 14α-hydroxy-8,19-oxido-20β-pivaloxy-pregn-4,6-dien-3-one had been formed.

EXAMPLE 38

A mixture of 20 mg of 19-hydroxy-8β,14β-oxido-20β-pivaloxy-pregn-4,6-dien-3-one, as obtained in the preceding example, and 0.2 ml of glacial acetic acid was heated under nitrogen at 70° C. for 3.5 hours whereupon the mixture was evaporated at reduced pressure, yielding 14β-hydroxy-8,19-oxido-20β-pivaloxy-pregna-4,6-dien-3-one, as evidenced by tlc analysis.

EXAMPLE 39

A mixture of the product obtained in the preceding example, 1.0 ml of pyridine in 0.01 ml of thionyl chloride was left to stand at 0° C. for 5 minutes, whereupon part of said product was treated with ether and water. The ethereal phase was extracted four times with water and evaporated yielding a product consisting mainly of 8,19-oxido-20β-pivaloxypregna-4,6,14-trien-3-one, as verified by tlc analysis and comparison with the product obtained in Example 32 and 33.

EXAMPLE 40

A mixture of 20 mg of 3β-acetoxy-19-hydroxy-5α-pregn-8(14)-en-20-one, 0.4 ml of pyridine and 15.3 mg of pyridinium hydrobromide perbromide was stirred under nitrogen for 160 minutes at room temperature in absence of light whereupon 1.0 ml of a 0.5% aqueous solution of sodium bisulfite was added, followed by 2 ml of ether. The organic phase was extracted twice with 0.5 ml of water and evaporated at reduced pressure. The material obtained was then chromatographed on a silica gel G coated plate. Elution with ethyl acetate-benzene 1:6 gave a semi-solid which was recrystallized with pentane yielding 3β-acetoxy-8,19-oxido-5α-pregn-14-en-20-one as evidenced by the analysis and ir spectroscopy.

EXAMPLE 41

A mixture of 120 mg of 3β-hydroxy-8,19-oxido-5α-pregn-14-en-20-one tetrahydropyranyl ether, 0.6 ml of glacial acetic acid and 0.6 ml of water was concentrated at reduced pressure to approximately one half of its volume during 15 minutes while being heated externally by a water both heated to 72° C., whereupon 0.6 ml of glacial acetic acid-water 1:1 was added and the mixture was concentrated again as above for 5 minutes. Water was then added and the mixture was evaporated to dryness with intermittant addition of ample volumes of water and toluene. The solid residue, which consisted essentially of 3β-hydroxy-8,19-oxido-5α-pregn-14-en-20-one, was dried at high vacuum and then left to stand with 0.48 ml of pyridine and 0.24 ml of acetic anhydride for 16 hours under nitrogen, whereupon 7.2 ml of water was added. Filtration yielded 98.9 mg of 3β-acetoxy-8,19-oxido-5α-pregn-14-en-20-one.

EXAMPLE 42

A mixture of 75 mg of 3β-hydroxy-8,19-oxido-20β-pivaloxy-5α-pregn-14-ene, 0.225 ml of pyridine and 0.075 ml of acetic anhydride was heated under nitrogen at 84° C. for 30 minutes, whereupon 3 ml of water was added. Filtration, followed by extensive washing of the precipitate in the water and drying at high vacuum yielded 3β-acetoxy-8,19-oxido-20β-pivaloxy-5α-pregn-14-ene, ir (nujol) 3056, 1729, 1722, 1285, 1252, 1212 and 1165 cm$^{-1}$.

EXAMPLE 43

To 10 ml of 97% formic acid, which was cooled by an ice bath and protected from moisture by an atmosphere of dry nitrogen, was added 20 ml of acetic anhydride with stirring. The mixture was heated to 50° C. for 15 minutes and then cooled to 0°. A mixture of 0.075 ml of the above solution, 25 mg of 3β-hydroxy-8,19-oxido-20β-pivaloxy-5α-pregn-14-ene and 0.075 ml of pyridine was then left to stand under nitrogen at room temperature for 50 minutes, whereupon 1.0 ml of water was added. The mixture was filtered, the precipitate was washed extensively with water and dried yielding 22 mg of 3β-hydroxy-8,19-oxido-20β-pivaloxy-5α-pregn-14-ene 3-formate, ir (nujol) 3050, 1279, 1180, 1170 and 1155 cm$^{-1}$.

EXAMPLE 44

A mixture of 80 mg of 3β-hydroxy-8,19-oxido-20β-pivaloxy-5α-pregn-14-ene and 1.6 ml of a solution, prepared from 5 volume of benzene and 1 volume of a 70% solution of sodium bis(1-methoxyethoxy)aluminum hydride in benzene, was stirred under nitrogen. After some stirring the mixture had formed a clear solution; after one hour another 1.6 ml of the above solution was added. Stirring under nitrogen was continued for 1 hour, whereupon 0.4 ml of a 1% solution of aqueous sodium bicarbonate was added slowly, followed by one volume of benzene. The mixture was concentrated at reduced pressure, ethyl acetate was added and the process was repeated until the benzene had been replaced by ethyl acetate. The mixture was filtered through diatomaceous earth and the ethyl acetate in the filtrate was replaced by benzene by repeated concentration at reduced pressure to a small volume and addition of the latter solvent. One volume of pentane was then added; after standing at $-5°$ for 2 hours, the mixture was filtered yielding 38 mg of $3\beta,20\beta$-dihydroxy-8,19-oxido-$5\alpha$-preg-14-ene, as indicated by the analysis.

The latter product, 0.48 ml of pyridine, and 0.24 ml of acetic anhydride was left to stand under nitrogen for 18 hours, whereupon 7.2 ml of water was added. Filtration, followed by dissolution of the precipitate obtained in ether-ethylene dichloride 2:1, addition of 0.1 vol of pentane, addition of charcoal, filtration through diatomaceous earth, replacement of the solvents by pentane by repeated concentration at reduced pressure and addition of the latter solvent and filtration gave 27.9 mg of a crystalline precipitate of $3\beta$-diacetoxy-8,19-oxido-pregn14-ene, mp 188°–190° C., $[\alpha]^{25} = -9°$(C = 1.035, CHCl$_3$); ir (KBr) 1730, 1255, 1210, 1035, 1005 and 820 cm$^{-1}$, D. Hauser, K. Heusler, J. Kalvoda, K. Schaffner, and P. Jeger, Helv. Chim. Acta, 47, 1961 (1964) found for the same compound prepared by a different route mp 189°–190°, $[\alpha]^{20} = -7°$ (C = 1.035, CHCl$_3$).

EXAMPLE 45

A mixture of 10 mg of $3\beta$-acetoxy-19-hydroxy-$5\alpha$-pregn-8(14)-en-20-one 19-tetrahydropyranyl ether, 8 mg of metachloroperbenzoic acid and 10 ml of carbon tetrachloride was left to stand under nitrogen for 16 hours at $+5°$ C., whereupon it was extracted 3 times with 5 ml of 2% aqueous potassium hydroxide and once with water. Drying with sodium sulfate, followed by evaporation at reduced pressure gave a resinous material consisting essentially of the $8\alpha,14\alpha$-oxide of the starting material. A mixture of one third of the latter product, 3 ml of glacial acetic acid and 15 mg of 5% palladium on charcoal was then agitated in an atmosphere of hydrogen for 3 hours, whereupon one half of the mixture was diluted with ether, filtered through cotton and evaporated at reduced pressure to yield a product consisting essentially of $3\beta$-acetoxy-$14\alpha$-hydroxy-8,19-oxido-$5\alpha$-pregnan-20-one as indicated by tlc analysis.

EXAMPLE 46

Epoxidation of 12.3 mg of $3\beta$-acetoxy-19-hydroxy-$5\alpha$-pregn-8(14)-en-20-one when carried out by the procedure described in Example 45 gave a resinous material consisting of as the major product, $3\beta$-acetoxy-19-hydroxy-$8\beta,14\beta$-oxido-$5\alpha$-pregn-8(14)-en-20-one and of, as the minor product, $3\beta$-acetoxy-$14\alpha$-hydroxy-8,19-oxido-$5\alpha$-pregnan-20-one, as indicated by tlc analysis. The latter material when subjected to hydrogenation conditions as described in Example 2 gave a resinous material consisting of $3\beta$-acetoxy-$14\beta$-hydroxy-$5\alpha$-pregnan-20-one, as the major product and of the isomeric $14\alpha$-alcohol, as the minor product, as indicated by tlc analysis.

EXAMPLE 47

To a stirred mixture of 1 g of finely divided 19-hydroxy-$20\beta$-pivaloxypregna-4,6,8(14)-trien-3-one in 900 ml of carbon tetrachloride was added a freshly prepared solution of 800 mg of meta-chloroperbenzoic acid in 100 ml of carbon tetrachloride. After some stirring the initially turbid solution became clear; after some further stirring a precipitate formed; after 24 hours of stirring the precipitate was removed by filtration and washed repeatedly with carbon tetrachloride.

The filtrate was extracted 3 times with 2% aqueous potassium hydroxide and once with the same volume of water. It was then dried with sodium sulfate and evaporated at reduced pressure. Recrystallisation of the residue obtained with methylene chloride-hexane gave 197.8 mg of 19-hydroxy-$8\beta,14\beta$-oxido-$20\beta$-pivaloxypregna-4,6-dien-3-one, mp 167°–168° C. (sintering at 146°), uv (max) 286 m$\mu$, ir (KBr) 3430, 1720, 1660, 1620, 1575, 1280 and 1145 cm$^{-1}$.

The precipitate, which was obtained after filtration of the reaction mixture, was designated with methanol and methylene chloride to yield 210 mg of 19-hydroxy-$8\alpha$,1-$4\alpha$-oxido-$20\beta$-pivaloxypregna-4,6-dien-3-one as evidenced by tlc-analysis. The latter compound was further characterised as its 19-acetate as described in Example 10.

EXAMPLE 48

A mixture of 20 mg of 19-hydroxy-$8\beta,14\beta$-oxido-$20\beta$-pivaloxypregna-4,6-dien-3-one, 0.08 ml of pyridine and 0.04 ml of acetic anhydride was left to stand under nitrogen for 16 hours, whereupon 2.4 ml of water was added. After some standing the mixture was extracted with ether and the ethereal solution was extracted several times with water. Evaporation of reduced pressure yielded a resin, which solidified on treatment with pentane. Recrystallisation of the solid from petroleum ether-hexane gave 6.2 mg of 19-acetoxy-$8\beta,14\beta$-oxido-$20\beta$-pivaloxypregna-4,6-dien-3-one, mp 161°–163°, ir (KBr) 1735, 1720, 1670, 1620, 1615, 1285, 1250 and 1170 cm$^{-1}$.

EXAMPLE 49

A mixture of 10 mg of 19-hydroxy-$8\beta,14\beta$-oxido$20\beta$-pivaloxypregna-4,6-diene-3-one, 0.2 ml of acetic anhydride and 0.2 ml of pyridine was left to stand under nitrogen at room temperature for 16 hours, whereupon 2.0 ml of water was added. Filtration followed by recrystallisation of the precipitate obtained with methylene chloride-hexane gave 19-acetoxy-$8\alpha,14\alpha$-oxido-$20\beta$-pivaloxypregna-4,6-dien-3-one, ir (KBr) 1740, 1710, 1660, 1625, 1280, 1235 and 1170 cm$^{-1}$.

EXAMPLE 50

A mixture of 5 mg of 19-hydroxy-$8\beta,14\beta$-oxido-$20\beta$-pivaloxypregna-4,6-dien-3-one, 0.1 ml of ethyl acetate and 0.01 ml of water-sulfuric acid 2:1 was shaken at room temperature for 90 minutes, whereupon 0.2 ml of water and 0.5 ml of hexane were added. The organic phase was extracted 4 times with 0.2 ml of water and evaporated. The resinous residue obtained was digested with petroleum ether-hexane yielding, a white solid consisting of, $14\beta$-hydroxy-8,19-oxido-$20\beta$-pivaloxypregna-4,6-dien-3-one as evidenced by tlc analysis and ir spectroscopy.

EXAMPLE 51

A mixture of 20 mg of 19-hydroxy-8α,14α-oxido-20β-pivaloxypregna-4,6-dien-3-one, 0.4 ml of ethyl acetate, and 0.04 ml of water-sulfuric acid was stirred for 95 minutes at room temperature, whereupon 1.0 ml of water and 1.0 ml of hexane were added. The mixture was stirred at room temperature for 150 minutes and then filtered yielding 5.8 mg of 14α-hydroxy-8,19-oxido-20β-pivaloxypregna-4,6-dien-3-one, uv max 290 mμ, as indicated by the analysis. The analysis on a sample withdrawn before working up indicated that the reaction is already complete after 15 minutes.

EXAMPLE 52

A mixture of 7.5 mg of 14β-hydroxy-8,19-oxido-20β-pivaloxypregna-4,6-dien-3-one and 0.3 ml of methanol was cooled externally by an ice-bath. Then 2.5 mg of sodium borohydride was added. A sample withdrawn from the mixture after 30 minutes and rapidly diluted with a large volume of methanol showed uv max 247 mμ indicating that most of the starting material had been converted to 3β,14β-dihydroxy-8,19-oxido-20β-pivaloxypregna-4,6-diene. The reaction vessel was then filled with nitrogen and a suspension of 3 mg of 5% palladium on charcoal and 0.075 ml of methanol was added. The nitrogen was replaced by hydrogen and the mixture was shaken for 85 minutes at room temperature, whereafter the mixture was diluted with 3 ml of ether and filtered through a paper plug to remove the catalyst. The filtrate was evaporated at reduced pressure. The residue obtained was treated with methylene chloride and the mixture was filtered. Evaporation at reduced pressure gave a resin which was digested with pentane yielding a semi-solid consisting essentially of 3β,14β-dihydroxy-8,19-oxido-20β-pivaloxy-5α-pregnane as indicated by tlc analysis and ir spectroscopy.

EXAMPLE 53

A mixture of 1 g of 3β,19-dihydroxy-20β-pivaloxy-5α-pregn-8(14)-ene, 1000 ml of carbon tetrachloride and 900 mg of meta-chloroperbenzoic acid was left to stand at room temperature under nitrogen for 4 hours in the dark, whereupon it was extracted 3 times with 200 ml of 2% aqueous potassium hydroxide, once with 400 ml of water, dried with sodium sulfate and evaporated at reduced pressure to yield a white foam which was treated with pentane. The supernatant clear pentane solution was decanted and the residue was treated with ether, methylene chloride, and pentane, whereupon it solidified. Filtration yielded 717 mg of a material consisting of 3β,19-dihydroxy-8β,14β-oxido-20β-pivaloxy-5α-pregnane as the major product and 3β,14α-dihydroxy-8,19-oxido-20β-pivaloxy-5α-pregnane as the minor product as evidenced by tlc analysis.

EXAMPLE 54

A mixture of 300 mg of 3β,19-dihydroxy-8β,14β-oxido-20β-pivaloxy-5α-pregnane, 1.2 ml of acetic anhydride, and 2.4 ml of pyridine was left to stand at room temperature under nitrogen for 20 hours, whereupon 36 ml of water was added. The mixture was extracted with 72 ml of ether, the ethereal phase was extracted 3 times with 20 ml of water and evaporated at reduced pressure. The residue obtained was treated with methanol-water-pyridine 9:1:0.1, whereupon it solidified. The suspension was left to stand at −5° C. for one hour and then filtered. Yielding after drying, 146.8 mg of 3β,19-diacetoxy-8β,14β-oxido-20β-pivaloxy-5α-pregnane. The motherliquor, after evaporation, yielded a resin consisting mainly of 3β-acetoxy-14α-hydroxy-8,19-oxido-20β-pivaloxy-5α-pregnane.

EXAMPLE 55

A mixture of 5 mg of 3β,19-diacetoxy-8β,14β-oxido-20β-pivaloxy-5α-pregnane and 0.1 ml of 0.2N methanolic potassium hydroxide was left to stand at room temperature under nitrogen for 4 hours, whereupon 0.1 ml of 0.2N acetic acid in ethyl acetate was added. The mixture was then evaporated, yielding, as practically the only steroidal product, 3β,19-dihydroxy-8β,14β-oxido-20β-pivaloxy-5α-pregnane.

EXAMPLE 56

A mixture of 400 mg of a material, consisting of 3β,19-dihydroxy-8β,14β-oxido-20β-pivaloxy-5α-pregnane and 3β,14α-dihydroxy-8,19-oxido-20β-pivaloxy-5α-pregnane, 20 ml of glacial acetic acid was magnetically stirred in an atmosphere of hydrogen in the presence of Pd-C for 150 minutes, whereupon 60 ml of ether was added and the mixture was filtered through diatomaceous earth. The filtrate was cooled in an ice-bath and 80 ml of potassium hydroxide-water 3:1 was added with stirring. The organic phase was extracted twice with 15 ml of water, dried with sodium sulfate and evaporated at reduced pressure. Chromatography on silica gel G coated glass plte gave, on elution with ethyl acetate-benzene, 197 mg of 3β,14β-dihydroxy-8,19-oxido20β-pivaloxy-5α-pregnane as a semi-solid, ir (CHCl$_3$) 3605, 3555 (Sh), 1710, 1275, 1165, 1070, 1040, 1005 and 945 cm$^{-1}$, 120 mg of 3β,14α-dihydroxy-20β-pivaloxy-5α-pregnane, and 32 mg of 3β,14β,19-trihydroxy-20β-pivaloxy-5α-pregn-7-ene.

EXAMPLE 57

A mixture of 100 mg of 3β,14β-dihydroxy-8,19-oxido-20β-pivaloxy-5α-pregnane, 0.6 ml of benzene, 0.4 ml of benzene-dihydropyrane and 1.0 ml of benzene-phosphorous oxychloride 100:1 was left to stand under nitrogen at room temperature for 3 hours, whereupon 3 ml of 4% aqueous sodium bicarbonate was added in one lot. The mixture was extracted with 6 ml of ether and the ethereal phase was extracted twice with 30 ml of water to yield a resinous material consisting essentially of 3β,14β-dihydroxy-8,19-oxido-20β-pivaloxy-5α-pregnane 3-pyranyl ether, which was used in the reaction described in the subsequent example.

EXAMPLE 58

A mixture of 100 mg of 3β,14β-dihydroxy-8,19-oxido-20β-pivaloxy-5α-pregnane 3-tetrahydropyranyl ether and 5.0 ml of 0.2N methanolic potassium hydroxide was heated under nitrogen for 3 days in an oil bath, having a temperature of 69° C. At the end of the reaction some of the methanol had evaporated. The mixture was evaporated at reduced pressure with intermittent addition of benzene. The brown solid obtained was treated with water and ether. The ethereal solution was extracted twice with water and then hexane was added until some turbidity appeared. The turbid mixture was filtered through diatomaceous earth and the filtrate obtained was evaporated at reduced pressure. The residue obtained was treated with pentane, whereupon it solidified. Filtration gave 22 mg of 3β,14β,20β-trihydroxy-8,19-oxido-5α-pregnane 3-tetrahydropyranyl ether, as indicated by tlc analysis.

EXAMPLE 59

A mixture of the product obtained as described in the preceding Example and 3 ml of an approximately 11.7% solution of sodium bis(2-methoxyethoxy)aluminum hydride in benzene was stirred magnetically under nitrogen for 30 minutes at room temperature, whereupon 0.6 ml of 1% aqueous sodium bicarbonate was added slowly with stirring. The organic phase was decanted from the aqueous sludge which was washed 5 times with 1.5 ml of ethyl acetate. The combined organic phases were evaporated and the residue obtained was rinsed with pentane several times and then dried at high vacuum, yielding 84 mg of a semi-solid consisting essentially of 3β,14β,20β-trihydroxy-8,19-oxido-5α-pregnane 3-tetrahydropyranyl ether, which was used for the reaction described in the subsequent Example.

EXAMPLE 60

A mixture of 145 mg of 3β,14β,20β-trihydroxy-8,19-oxido-5α-pregnane 3-tetrahydropyranyl ether and 3.0 ml of pyridine was stirred under nitrogen in an ice-bath, 150 mg of chromium trixoide was then added slowly. After 20 minutes of stirring the ice-bath was removed and stirring was continued without external cooling for another 170 minutes, whereupon 0.15 ml of isopropanol was added. The mixture was diluted with 12 ml of methylene chloride and then filtered through approximately 1.5 ml of neutral aluminum oxide. The filtrate was evaporated at reduced pressure with intermittent addition of toluene. The residue obtained was dissolved in benzene and charcoal was added and the mixture was filtered through diatomaceous earth. The filtrate was concentrated at reduced pressure with intermittent addition of petroleum ether. Filtration yielded 51.6 mg of 3β,14β-dihydroxy-8,19-oxido-5α-pregnan-20-one 3-tetrahydropyranyl ether mp 132°-135° c., ir.

EXAMPLE 61

A mixture of 3 mg of 3β,14β-dihydroxy-8,19-oxido-5α-pregnan-20-one 3-tetrahydropyranyl ether and 0.5 ml of glacial acetic acid 1:1 was heated at 70° C. under nitrogen for 30 minutes, whereupon it was evaporated to one half of its volume by a stream of nitrogen. The remaining half was then evaporated with nitrogen and frequent intermittent addition of water yielding a resin consisting essentially of 3β,14β-dihydroxy-8,19-oxido-5α-pregnan-20-one as indicated by tlc analysis. A mixture of the latter product, 0.1 ml of acetic anhydride and 0.2 ml of pyridine was then heated at 84° C. under nitrogen for 30 minutes, whereupon 2 ml of water was added. The mixture was extracted with ether and the ethereal phase was evaporated at reduced pressure yielding a semi-solid consisting of 3β-acetoxy-14β-hydroxy-8,19-oxido-5α-pregnan-20-one as evidenced by tlc analysis.

EXAMPLE 62

To a solution, which was protected by a nitrogen atmosphere, of 0.0935 ml of ethoxyacetylene in 5.6 ml of absolute ether, which had been dried over molecular sieves (4 Angstrom), was added 0.56 ml of 1.95 M solution of methyl lithium in ether. The mixture thus prepared was then added to a solution of 23 mg of 3β,14β-dihydroxy-8,19-oxido-5α-pregnan-20-one 3-tetrahydropyranyl ether in 3.32 ml of absolute ether, which also was protected by an atmosphere of nitrogen. The mixture was then stirred under nitrogen for 19 hours, whereupon one volume of ice-water was added, followed by one volume of ether. The mixture was extracted twice with water, dried with sodium sulfate and evaporated at reduced pressure yielding a resin consisting essentially of 3β,14β,20-trihydroxy-20-ethoxyethinyl-8,19-oxido-5α-pregnane. A mixture of the latter product, 2.3 ml of absolute ethanol and 0.56 ml of 2N aqueous sulfuric acid was stirred magnetically under nitrogen for 85 minutes, whereupon 10 volumes of ice-water were added and the mixture was extracted 5 times with 5.6 ml of methylene chloride. The combined methylene chloride extracts were extracted with an excess of aqueous sodium bicarbonate solution, dried with sodium sulfate and then evaporated yielding a resin consisting essentially of 3β,14β-dihydroxy-8,19-oxido-5α-norchol-20-enic acid ethyl ester, uv max 230 mμ. The latter product was then left to stand with 0.6 ml of pyridine and 0.3 ml acetic anhydride under nitrogen for 16 hours at room temperature, whereupon 10 volumes of water were added. Extraction with ether, followed by extraction of the ethereal phase with water and evaporation at reduced pressure gave a product which was chromatographed on a silica gel G coated plate. Elution with ethyl acetate-benzene 1:4 gave 10 mg of a colourless resin consisting of 3β-acetoxy-14β-hydroxy-8,19-oxido-5α-norchol-20-enic acid ethyl ester uv max 231 mμ as evidenced by tlc analysis.

EXAMPLE 63

A mixture of 35 mg of 3-tetrahydropyranyloxy-8,19-oxido-20-oxo-5α-pregn-14-ene, 0.35 ml of acetic anhydride and 0.35 ml of acetic acid was treated under nitrogen at 70° C. for 24 hours, whereupon it was concentrated at reduced pressure to yield a semi-solid, which was recrystallised from ether-methylene chloride-hexane and ether-hexane to yield 3β-acetoxy-8,19-oxido-5α-pregn-14-en-20-one, ir (KBr) 3070, 1730, 1690, 1240, 1030, 1005 and 820 cm$^{-1}$. The mother liquor contained, besides the above product, a less polar compound as indicated by tlc, which has uv max 245 mμ, and was considered to be 3β,19-diacetoxy-5α-pregna-9,14-dien-20-one or the isomeric 7,14-diene.

EXAMPLE 64

A mixture of 17.1 ml of benzene, 1.530 g of lead tetraacetate, a solution of 300 mg of 20-oxo-8,19-oxido-5α-pregn-14-en-3β-yl 2'-tetrahydropyranyl ether in 17.1 ml of benzene and a freshly prepared solution of 5.04 ml of boron trifluoride etherate in 1.62 ml of methanol, was stirred at room temperature. After a few minutes a brown tar precipitated from the solution. After 4 hours of stirring the supernatant solution was filtered, diluted with ethyl acetate, extracted 8 times with 20 ml of water, dried with sodium sulfate and concentrated at reduced pressure. The resin obtained, when treated with ether-pentane, yielded 149.4 mg of a crystalline precipitate of crude product, mp 150–152 (sintering at 105°), recrystallisation from ether gave the purified sample of 21-acetoxy-3β-hydrody-8,19-oxido-5α-pregn-14-en-20-one, mμ 168, 172°-172.5° C., ir (nujol) 3360 (broad), 3050, 1742, 1718 and 1240 cm$^{-1}$.

EXAMPLE 65

A mixture of 40 mg of 21-acetoxy-3β-hydroxy-8,19-oxido-5α-pregn-14-en-20-one and 0.8 ml of methanol was stirred magnetically under nitrogen until all material had dissolved, whereafter 0.040 ml of 2% aqueous potassium hydroxide was added. The basic mixture was stirred for one hour at room temperature, 0.070 ml of ethyl acetate-acetic acid 100:2 was added and the mixture was concentrated to a small volume at reduced pressure. Hexane was added and the mixture was concentrated again. The clear supernatant solution was then decanted. Treatment of the residue with ether, followed by filtration gave 10 mg of 3β,21-dihydroxy-8,19-oxido-5α-pregn-14-en-20-one, ir (KBr), 3400 (broad), 3050 (shoulder), 1712, 1080, 1048, 1020 and 1000 cm$^{-1}$.

EXAMPLE 66

To a mixture of 1.2 g of 3β,21-diacetoxy-8,19-oxido-5α-pregn-14-en-20-one was added 6.0 ml of 2% aqueous potassium hydroxide-methanol 1:9. The mixture was stirred under nitrogen for 5 hours, whereupon 0.6 ml of acetic acid-ethyl acetate 2:1000 was added. Evaporation at reduced pressure, followed by dissolution of the organic material with ether-methylene chloride, several extractions of the organic phase with ¼ saturated aqueous sodium bicarbonate, extraction with water, drying with sodium sulfate, concentration at reduced pressure with intermittant addition of hexane, cooling at −5° for 16 hours and filtration gave 1.05 g of 3β-acetoxy-21-hydroxy-8,19-oxido-5α-pregn-14-en-20-one, mp 192°–194.5° C.

EXAMPLE 67

A mixture, prepared by successive addition of 120 mg of 3β,19-dihydroxy-20β-pivaloxy-5α-pregn-8(14)-ene, 1.2 ml of methylene chloride and 81 mg of iodine was stirred under nitrogen for 2.5 hours, whereupon 3 ml of aqueous sodium bicarbonate and 6 ml of ether was added. The organic phase was extracted with aqueous sodium bisulfite, then with water, dried with sodium sulfate and evaporated yielding a mixture of 3β-hydroxy-8,19-oxido-20β-pivaloxy-5α,14αor 14β-pregnane and 3β-hydroxy-8,19-oxido-20β-pivaloxy-5α-pregn-14-ene as evidenced by tlc-analysis. The mixture was separated by chromatography on silica gel G coated glass plates, using ethyl acetate-benzene 1:1 as the eluant. The structure of the former compound was then verified by a comparison of its nmr spectrum with that of the 14-dehydro analog.

EXAMPLE 68

To a mixture of 83.6 ml of benzene, 3.74 g of lead tetraacetate and 2 g of 3β-acetoxy-8,19-oxido-5α-pregn-14-en-20-one was added a freshly prepared solution of 12.12 ml of boron trifluoride etherate in 3.94 ml of methanol. The mixture was stirred for 2 hours at room temperature. Dilution with 83.6 ml of ethyl acetate, repeated extraction of the organic phase with water, drying of the organic phase with sodium sulfate and evaporation gave a foam, which after digestion with ether-pentane 1:2 at −5° and filtration gave 1.5 g of 3β,21-diacetoxy-8,19-oxido-5α-preng-14-en-20-one, mp 147, 152°–153.5° C.

The mother liquor of the latter precipitate was combined with those obtained in previous runs of the same reaction and chromatographed on silica gel G coated thin layer plates. Elution with ethyl acetate-benzene 1:4 gave a fraction which after evaporation and recrystallisation of the residue obtained with ether-pentane gave 3β-acetoxy-21-methoxy-5α-pregn-14-en-20-one, nmr (CDCl$_3$, δ) 5.68 (m, 15-position), 4.68 (m, 3-position), 4.02 (t, 21-position), 3.85 (centre of perturbed double d, 19-position), 3.42 (s, 21-methoxy), 2.01 (s, 3-acetate) and 1.01 (s, 18-position); mass-spectrum (70 ev) m/e 402 (strong), 387 (medium), 372 (medium), 371 (medium), 357 (medium), 342 (strong).

EXAMPLE 69

A mixture prepared by successive addition of 2.0 ml of methylene cloride, 0.5 ml of pyridine and 200 mg of pyridinium bromide perbromide to 250 mg of 19-hydroxy-20β-pivaloxy-5α-pregn-14-ene was stirred at room temperature and under nitrogen in the dark for 2 hours whereupon 6.25 ml of 4% aqueous sodium bisulfite was added. Stirring was continued for several minutes and 1.0 ml of concentrated hydrochloric acid-water 1:10 was added. Extraction with ether, followed by several extractions of the organic phase with water, drying with sodium sulfate, evaporation at reduced pressure and recrystallisation with ether-methanol afforded 8,19-oxido-20β-pivaloxy-5α-pregn-14-ene in two crops, 112 mg, mp 165°–167° C., and 34.4 mg, mp 160°–162° C., respectively.

EXAMPLE 70

A mixture, prepared by addition of a suspension of 200 mg of palladium in 5 ml of acetic acid to a solution of 400 mg of 19-hydroxy-8β,14β-oxido-20β-pivaloxy-5α-pregnane in 5 ml of acetic acid, was stirred in an atmosphere of hydrogen for 2½ hours, whereupon the hydrogen was replaced by nitrogen and 100 ml of ether was added. Filtration through diatomaceous earth, two extractions of the filtrate with 100 ml of water one extraction with 25 ml of 10% aqueous potassium hydroxide, subsequent extraction with water till the aqueous extracts were no longer basic, drying with sodium sulfate and evaporation at reduced pressure gave a solid which after dissolution in methanol, precipitation with water and filtration gave 326 mg of 14β-hydroxy-20β-pivaloxy-8,19-oxido-5α-pregnane, 134, 138°–141° C., which had an it-spectrum identical to the product of the subsequent reaction.

EXAMPLE 71

A mixture of 10 mg of 19-hydroxy-8β,14β-oxido-20β-pivaloxy-5α-pregnane and 0.4 ml of 90% aqueous formic acid was shaken under nitrogen for 16 hours, whereupon 1 vol of water was added. Filtration of the resulting suspension gave 14β-hydroxy-20β-pivaloxy-8,19-oxido-5α-pregnane, 134, 138°–141° C.

EXAMPLE 72

A solution of 1 mg of 19-hydroxy-8β,14β-oxido-20β-pivaloxy-5α-pregnane in 0.075 ml of toluene, was shaken with 0.075 ml of 70% perchloric acid-water 1:10 for 16 hours, whereupon the mixture was extracted with aqueous sodium bicarbonate solution. Evaporation of the organic phase gave 14β-hydroxy-20β-pivaloxy-8,19-oxido5α-pregnane, as evidenced by tlc.

EXAMPLE 73

A mixture of 1.39 g of 19-hydroxy-20β-pivaloxy-5α-pregn-8(14)-ene, 139 ml of hexane and 0.834 g of metal-chloroperbenzoic acid was stirred in the dark under nitrogen for 4 hours and 40 minutes, whereupon 13.6 ml of methylene chloride was added and the mixture was extracted 3 times with 41.7 ml of 2% aqueous potassium hydroxide and then with water till the aqueous extracts were neutral. Drying with sodium sulfate, followed by evaporation at reduced pressure and recrystallization from ether-pentane gave 0.980 g of 19-hydroxy-8β,14β-oxido-20β-pivaloxy-5α-pregnane, mp 162°–167°. The mother liquor contained 14α-hydroxy-8,19-oxido-20α-pivaloxy-5α-pregnane as the major product as evidenced by tlc.

EXAMPLE 74

Treatment of 4.5 g of 8,19-oxido-20β-pivaloxy-5α-pregn-14-ene under conditions similar to those described in Example 59 for the liberation of the 20β-hydroxy group in the corresponding 3β-tetrahydropyranyloxy analog, gave 3.08 of 20β-hydroxy-8,19-oxido-5α-pregn-14-ene, mp 122°–124° C., after recrystallisation from ether-pentane.

EXAMPLE 75

Oxidation of 3 g of 20β-hydroxy-8,19-oxido-5α-androst-14-ene under conditions similar to those described in Example 60 for the oxidation of the corresponding 3β tetrahydropyranyloxy analog, gave 2.361 g of 8,19-oxido-5α-pregn-14-en-20-one, mp 171, 172°–174° C., ir(KBr) 3048,1705, 1489, 1450, 1376, 1357, 1291, 1280, 1232, 1208, 1190, 1147, 1022, 1008, 928, 910, 889, 857, 816, 802, 795, 746 and 608 cm$^{-1}$, after recrystallisation of the crude product from methylene chloridepentane.

EXAMPLE 76

Acetoxylation of 2.5 g of 8,19-oxido-5α-pregn-14-en-20-one under conditions similar to those described in Example 68 gave 1.78 g of 21-acetoxy-8,19-oxido-5α-pregn-14-en-20-one, mp 163–165.5 after recrystallisation of the crude product from benzene-pentane.

The combined mother liquors of several runs where chromatographed on silica gel G coated glass plates with ethyl acetate-benzene 1:7 as the eluant. Dissolution of the fraction, rf = 0.25, in ether, addition of hexane till the solution became turbid, filtration through diatomaceous earth, evaporation of the filtrate, and two recrystallisations of the residue obtained from methanol-water gave 21-methoxy-8,19-oxido-5α-pregn-14-en-20-one, m/1 344 (strong, m), 329 (m-15) and 313 (m-31).

EXAMPLE 77

Oxidation of 75 mg of 3β-hydroxy-8,19-oxido-20β-pivaloxy-5β-pregn-14-ene under conditions similar to those described in Example 60 gave a product, which after two recrystallisations from methanol-water afforded 8,19-oxido-20β-pivaloxy-5α-pregn-14-en-3-one.

A mixture of 25 mg of the latter ketone, 0.250 ml of hydrazine, 0.250 ml of ethylene glycol and 50 mg of potassium carbonate was then heated in a closed tube under nitrogen at 150°–170° C. for 20 hours, whereupon 1.0 ml of water was added. Extraction with ethyl acetate, followed by several extractions of the organic phase with water and evaporation gave a white brittle foam consisting mainly of 20β-hydroxy-8,19-oxido-5α-pregn-14-ene as evidenced by tlc.

When 16 mg of the latter 20β-alcohol were oxidized under conditions similar to those described in Example 60, chromatography of the crude product on silica gel G coated glass plates with ethyl acetate-benzene 1:7 as the eluant and recrystallisation of the fraction collected from ether-hexane, gave 8,19-oxido-5α-pregn-14-en-20-one, mp 171°–176° C., which had an ir spectrum identical to that of the 20-ketone obtained in Example 75.

EXAMPLE 78

Hydrolysis of 950 mg of 21-acetoxy-8,19-oxido-5α-pregn-14-en-20-one under conditions which were essentially the same as those described in Example 66 for the corresponding 3-acetoxy analog gave 809 mg of 21-hydroxy-8,19-oxido-5α-pregn-14-en-20-one, mp 162, 164–166.5, 171°, m/1 330 (m), after precipitation of the crude product from ethyl acetate-acetic acid-water.

The mother liquor of several runs afforded 8,19-oxido-5α-androst-14-en-17β-carboxylic acid, m/1 316, 298, 245 and 232 after extraction with aqueous potassium hydroxide and acidification of the basic extracts with mineral acid.

EXAMPLE 79

A solution of 5 mg of 21-hydroxy-8,19-oxido-5α-pregn-14-en-20-one in 0.250 ml of isopropanol was protected by an atmosphere of nitrogen, whereupon 0.25 ml of isopropanol — 2% aqueous potassium hydroxide 4:1 was added. The mixture was stirred for 90 minutes and 0.125 ml of the same alkaline solution was added. After 5 hours of total stirring time the mixture was left to stand at −5° for 16 hours, whereupon an excess of ethyl acetate-acetic acid 100:2 was added. Evaporation at reduced pressure, followed by dissolution in ether-methylene chloride 4:1, extraction with water and evaporation of the organic phase gave a white solid consisting mainly of 8,19-oxido-5α-androst-14-en-17β-carboxylic acid, as evidenced by tlc comparison with the acid obtained in Example 78.

EXAMPLE 80

To a mixture which was protected by an atmosphere of nitrogen, of the carboxylic acid obtained in Example 78, and 0.3 ml of tetrahydrofuran was added 6 mg of lithium aluminum hydride. The mixture was taken at room temperature for 4 days. It was then cooled in an ice-bath and 1.0 ml of wet ether was added dropwise, followed by 3 drops of water. The volatile components of the mixture were then evaporated at reduced pressure and the resulting cake was extracted with methanol-ethyl acetate 1:1, filtration, followed by evaporation, chromatography on silica gel G coated glass plates with ethyl acetate-benzene 1:4 as the eluant, gave 17β-hydroxymethyl-8,19-oxido-5α-androst-14-ene m/e 302 (m), 271 (m-31), which had an ir spectrum identical to that of the product obtained in Example 81.

EXAMPLE 81

Reduction of crude 21-hydroxy-8,19-oxido-5α-pregn-14-en-20-one with lithium aluminum hydride under conditions similar to those described in Example 80 followed by chromatography on silica gel G coated glass plates, with ethyl acetate benzene 1:1 as the eluant, gave a fraction which after recrystallisation from ether-hexane yielded a precipitate of 20, 21-dihydroxy-8,19-oxido-5α-pregn-14-ene ad evidenced by thin layer chromatography.

A mixture of 4 mg of the latter diol, 0.4 ml of benzene and 12 mg of lead tetraacetate was then agitated in an atmosphere of nitrogen for 90 minutes, whereupon it was diluted with ether and water was added. The ethereal phase was extracted 3 times with ½ volume of water and evaporated yielding a white solid consisting essentially of 17β-formyl-8,19-oxido-5α-androst-14-ene, as evidenced by tlc analysis.

Reduction of 3 mg of the latter product in 0.3 ml of methanol with 0.6 mg of sodium borohydride under nitrogen, followed by quenching of the reaction with acetic acid-water 1:10, extraction with ether-methylene chloride 4:1, chromatography on silica gel G coated glass plates with ethylacetate-benzene 1:4 as the eluant and recrystallisation of the isolated fraction with methylene chloride gave 17β-hydroxymethyl-8,19-oxido-5α-androst-14-ene, mp 141–142, ir(KBr) 3380, 3050, 2980, 2920, 2845, 1482, 1452, 1441, 1365, 1205, 1189, 1042, 1030, 1010, 1000, 988, 965, 929, 905, 855, 814, 799 and 792 in cm$^{-1}$. The ir spectrum was identical to that of the product obtained in Example 80. The identity of both compounds was also shown by thin layer chromatography.

EXAMPLE 82

A suspension of 137 mg of 14β-hydroxy-8,19-oxido-20β-pivaloxy-5α-pregnane and 2.74 ml of 2N methanolic potassium hydroxide was shaken under nitrogen at 67° to 70° C. for 20 hours whereupon all suspended material had dissolved and 27.4 ml of water was added. Extraction with ether-methylene chloride, extraction of the organic phase with water till the aqueous extracts were neutral and evaporation gave a white solid which on digestion with pentane and filtration yielded 82 mg of 14β,20β-dihydroxy-8,19-oxido-5α-pregnane, mp 172, 129–129.5, m/e 334(m), 316(m-18).

EXAMPLE 83

To 46 mg of 14β,20β-dihydroxy-8,19-oxido-5α-pregnane was added 2.76 ml of carbon tetrachloride, 0.46 ml of t-butanol and 0.552 ml of a solution of t-butyl chromate in carbon tetrachloride; the latter solution was 1.85 normal with respect to chromium ions and was prepared as outlined by K. Heusler and A. Wettstein, Helvetica Chimica Acta, 35, 284 (1952) p. 282.

The mixture was stirred for 68 hours whereupon it was left to stand with methanol. Subsequent evaporation, followed by dissolution of the residue in methylene chloride, filtration through diatomaceous earth, evaporation of the filtrate and digestion of the white solid obtained with pentane gave 36.9 mg of 14β-hydroxy-8,19-oxido-5α-pregnan-20-one, nmr (CDCl$_3$, δ) 3.79 (d of d, J=8cps, 2) 3.61 (s, 1, disappears with D$_2$O), 2.6–2.9(m, 1), 2.26 (s, 3) and 1.12 (s, 3).

EXAMPLE 84

To a solution, which was protected by an atmosphere of nitrogen, of 5 mg of 14β-hydroxy-8,19-oxido-5α-pregnan-20-one in 0.87 ml of tetrahydrofuran was added a solution consisting of 1.12 ml of tetrahydrofuran, 0.0225 ml (0.321 millimoles) of ethoxyacetylene and 0.112 ml of a 1.95 molar solution of methyl lithium in ether. The mixture was stirred magnetically for 2 hours and then evaporated. Treatment of the residue with ether, followed by four extractions of the ethereal phase with water and evaporation at reduced pressure gave a resin containing 14β,20ε-dihydroxy-b 20ε-ethyoxyethynyl-8,19-oxido-5α-pregnane as essentially the only steroidal product, as evidenced by tlc.

Treatment of the latter product in methanol with 2N aqueous sulfuric acid, followed by dilution with water, extration with ether and four extractions of the ethereal phase with water gave a resinous product, uv max 229 mμ, consisting of ethyl 14β-hydroxy-8,19-oxido-5α-norchol-20(22)-enate as the major steroidal product, as evidenced by tlc and the uv-spectrum.

When 5 mg of the isomeric 14β-hydroxy-8,19-oxido-5β-pregnan-20-one was treated with ethoxy acetylene and methyl lithium 14β,20ε-dihydroxy-20ε-ethoxyethynyl-8,19-oxido-5β-pregnane was similarly obtained. Treatment of the latter compound with aqueous sulfuric acid in methanol as described above for the 5α-isomer gave ethyl 14β-hydroxy-8,19-oxido-5β-norchol-20(22)-enate, uv max 229 mμ as evidenced by tlc analysis.

EXAMPLE 85

Hydrogenation of 19-hydroxy-20β-pivaloxy-pregna-4,6,8(14)-trien-3-one under conditions which were essentially the same as those outlined in Example 15 of U.S. Pat. No. 3,849,402, issued Nov. 19, 1974, except that part of the t-butylamine used was substituted by ethyl acetate, gave 19-hydroxy-20β-pivaloxy-5βL-pregn-8(14)-en-3-one as the major product and the corresponding 5α-isomer as a minor product. Recrystallisation and subsequent acetylation under standard condition with acetic anhydride and pyridine gave the corresponding 19-acetate of the 5β-isomer which was contaminated by a small amount of the 19-acetate of the 5α-isomer.

A mixture of 2.5 g of the above product, 75.0g of zinc, 187.5 ml of methylene chloride and 62.5 ml of 90% aqueous formic acid was shaken overnight at room temperature, whereupon the zinc was removed by filtration. The filtrate was then combined with the filtrates of two identical runs and the mixture was concentrated at reduced pressure with intermittant addition of hexane and water. Filtration, followed by recrystallisation of the collected precipitate from methanol-water gave 0.92 g of 19-acetoxy-20β-pivaloxy-5β-pregn-8(14)-ene, mp 120°–121.5° C. The latter product was also obtained when the starting ketone was converted to the corresponding 3-tosyl-hydrazone by treatment with tosyl hydrazine in benzene and subsequent treatment of the hydrazone with sodium borohydride in methanol.

Selective hydrolysis of the product obtained by the above zinc-treatment with 0.5 N methanolic potassium hydroxide gate 19-hydroxy-20β-pivaloxy-5β-pregn-8(14)-ene as the major product and left the 19-acetoxy analog of the 5α-series unaffected. Precipitation with water, followed by recrystallisation from pentane gave the purified major product, 131°–132° C. which was practically uncontaminated by compounds of the 5α-series.

Oxidative cyclisation of 4.0 g of the latter 19-hydroxy-8(14)-ene under conditions similar to those described in Example 69, except that the extraction with aqueous hydrochloric acid was omitted, gave 3.63 g of 8,19-oxido-20β-pivaloxy-5β-pregn-14-ene, mp 122°–124° C., after recrystallisation of the crude product from ethyl acetate-methanol-water 12:138:110.

EXAMPLE 86

Treatment of 3.3 g of 8,19-oxido-20β-pivaloxy-5β-pregn-14-ene under conditions similar to those described in Example 59 for the liberation of the 20β-OH group gave a crude product consisting essentially of 20β-hydroxy-8,19-oxido-5β-pregn-14-ene.

The latter crude 20β-alcohol was then oxidized under conditions similar to those described in Example 60 yielding 2.129 g of 8,19-oxido-5β-pregn-14-en-20-one, mp 134°–135° C.

Another route to the latter compound commenced with the treatment of 19-hydroxy-20β-pivaloxy-5β-pregn-8(14)-en-3-one under the conditions of the Wolff- Kishner reaction similar to those outlined in Example 77 except that potassium hydroxide instead of potassium carbonate was used. Subsequent oxidative cyclisation of the resulting 19,20β-dihydroxy-5β-pregn-8(14)-ene, m/e 318(m), 300 (m-18), 387(m-31) and 369(m-49), to the corresponding 20β-hydroxy-8,19-oxido-14-ene under conditions similar to those outlined in Example 69, and oxidation of the latter 20β-alcohol under conditions similar to those outlined in Example 60 gave 8,19-oxido-5β-pregn-14-en-20-one nmr (CDCl$_3$, δ), 5.6–5.75(m, 1) 3.68(s, 2), 2.15(s, 3) and 1.0 (s, 3).

EXAMPLE 87

Acetoxylation of 250 mg of 8,19-oxido-5β-pregn-14-en-20-one under conditions similar to those described in Example 68 gave 147.2 mg of 21-acetoxy-8,19-oxido-5β-pregn-14-en-20-one, mp 122.5°–127.5° C., after recrystallisation of the crude product from methanol-water. The reaction also afforded a more polar by-product which was considered to be 21-methoxy-8,19-oxido-5β-pregn-14-en-20-one.

A mixture of 135 mg of the above 21-acetate, 27 ml of methanol and 2.7 ml of half-saturated aqueous sodium bicarbonate was stirred under nitrogen for 1.5 hours, whereupon a sample was taken, neutralized with acetic acid, evaporated and analyzed by tlc. Subsequently 1.35 ml of a second lot of the half-saturated sodium bicarbonate solution was added. After 3.5 hours of base-treatment 6.75 ml of ethyl acetate-acetic acid 100:2 was added. Evaporation at reduced pressure, followed by treatment of the residue with ether-methylene chloride 4:1, extraction of the organic phase with water, evaporation of the organic phase and crystallisation of the residue from pentane gave 90.25 mg of 21-hydroxy-8,19-oxido-5β-pregn-14-en-20-one, mp 128°–130° C., ir (KBr) 3470, 3061, 1705, 1452, 1443, 1372, 1350, 1285, 1263, 1205, 1182, 1066, 1000, 902, 888, 860 and 909 cm$^{-1}$.

EXAMPLE 88

A mixture of 1 g of 19-hydroxy-20β-pivaloxy-5β-pregn-8(14)-ene and a small amount of hexane was stirred under nitrogen till a thick paste had formed; then hexane was added in an amount to bring the total volume to 100 ml. Most of the steroid has then dissolved. Similarly a suspension of 600 mg metachloroperbenzoic acid in 50 ml of hexane was prepared and then added to the steroid. The mixture was stirred under nitrogen in absence of light for 215 minutes whereupon it was extracted three times with 60 ml of 2% aqueous potassium hydroxide in a nitrogen atmosphere. Drying of the organic phase over sodium sulfate followed by evaporation and two recrystallisations of the residue from hexane gave 322.96 mg of 19-hydroxy-8β,14β-oxido-20β-pivaloxy-5β-pregnane, mp 111°–113° C. The mother liquors consisted essentially of the latter product and of the isomeric 14α-hydroxy-8,19-oxido-20β-pivaloxy-5β-pregnane.

EXAMPLE 89

Oxidation of 209 mg of 19-hydroxy-20β-pivaloxy-5β-pregn-8(14)-ene by the method described in the preceding Example gave the crude product as a foam which was left to stand with 8 ml of pentane under nitrogen at −5° C. for 2.5 days and was seeded with 14α-hydroxy-8,19-oxido-20β-pivaloxy-5β-pregane. A small precipitate had formed in which the 14α-hydroxy-8,19-oxide was enriched. Filtration, followed by evaporation of the filtrate gave 142.76 mg of a glassy resin consisting mainly of 19-hydroxy-8β,14β-oxido-20β-pivaloxy-5β-pregnane and a smaller amount of the isomeric 14α-hydroxy-8,19-oxide.

Treatment of the latter mixture of compounds with 2.85 ml of 90% aqueous formic acid under nitrogen in the dark followed by addition of 5.7 ml of water and filtration gave 123 mg of a precipitate consisting of 8,19-oxido-14β-hydroxy-20β-pivaloxy-5β-pregnane and a small amount of the isomeric 14α-hydroxy isomer.

A suspension of 78 mg of the latter compound in 3.9 ml of 2N methanolic potassium hydroxide, which was protected by an atmosphere of nitrogen, was then gently shaken in a heating bath at 62° C. After 45 minutes all solid material had dissolved; after 4.5 hours of heating 0.52 ml of acetic acid was added and the mixture was evaporated at reduced pressure. Treatment of the residue with hexane-methylene chloride 4:1, followed by extraction of the organic phase with water, drying with sodium sulfate, filtration through diatomaceous earth and evaporation gave 70.75 mg of a resin, which, after chromatography in silica gel G coated glass-plates with ethyl acetate-benzene 1:4 as the eluant, gave 47.63 mg of a fraction consisting of 14β,20β-dihydroxy-8,19-oxido-5β-pregnane and 20 mg of a less polar fraction consisting mainly of unreacted 14α-hydroxy-8,19-oxido-20β-pivaloxy-5β-pregnane.

Oxidation of 42 mg of the 14β,20β-diol under conditions similar to those described in Example 83 gave 33.8 mg of 14β-hydroxy-8,19-oxido-5β-pregnan-20-one, mp 113°–114° C.

EXAMPLE 90

To a stirred mixture, protected from light and by an atmosphere of nitrogen, and cooled by an ice-water bath, of 150 mg of 3β-acetoxy-19-hydroxy-20β-pivaloxy-5α-pregn-14-ene and 6.0 ml of acetone was added a solution of 120 mg of N-bromosuccinimide in 3.0 ml of water. After 2 hours 6.0 ml of a half-saturated aqueous solution of sodium bisulfite and 90 ml of ice-cold water was added. The mixture was stirred for another 50 minutes in the ice-bath and was then filtered. The precipitate collected was dried at high vacuum overnight and left to stand with 3.0 ml of t-butylamine for 10 minutes under nitrogen. Subsequent evaporation at reduced pressure, followed by treatment with petroleum ether, standing at −5° C. under nitrogen overnight and filtration gave 96.65 mg of a precipitate containing 3β-acetoxy-15ξ-bromo-14ξ-hydroxy-8,19-oxido-20β-pivaloxy-5α-pregnane as the major product and a small amount of 3β-acetoxy-19-formyloxy-14β,15β-oxido-20β-pivaloxy-5α-pregnane. Chromatography of the precipitate on silica gel G coated glass plates with ethyl acetate-benzene 1:7 as the eluant gave a fraction which after crystallisation from pentane gave 15.3 mg of the purified sample, of the major product, mp 188–191 (dec), m/e 554, 556 (chemical molecular weight 555), ir (KBr) 3495, 2945, 2870, 1730, 1698, 1480, 1365, 1289, 1256, 1182, 1170, 1033, 998, 993, 927, 868 and 774 cm$^{-1}$.

When approximately 5 mg of the above compound was shaken with 150 mg of zinc dust, 0.375 ml of toluene and 0.125 ml of 90% aqueous formic acid, filtration, washing of the precipitate with benzene-methylene chloride 1:1 and evaporation gave a product containing 3β-acetoxy-19-formyloxy 20β-pivaloxy-5α-pregn-14-ene as the major steroidal product and a smaller amount of the corresponding 19-alcohol, as evidenced by tlc-analysis. When a mixture consisting of 2.5 mg of the 14ξ,15ξ-bromohydrin, 0.5 ml of methylene chloride, 0.05 ml of pivalic acid-methylene chloride 1:10 and wet Raney nickel, prepared from 150 mg of nickel-aluminium alloy 1:1, was shaken overnight at room temperature, filtration, dilution of the filtrate with ether, extraction of the organic phase with half-saturated bicarbonate solution and evaporation gave a product consisting mainly of 3β-acetoxy-8,19-oxido-20β-pivaloxy-5α-pregn-14-ene, as evidenced by tlc analysis.

EXAMPLE 91

Treatment of 25 mg of 19-hydroxy-20β-pivaloxy-5α-pregn-8(14)-ene with N-bromosuccinimide under conditions similar to those described in the preceding Example gave a crude product consisting essentially of 8,19-oxido-20β-pivaloxy-5α-pregn-14-ene, as evidenced by tlc analysis.

I claim:
1. A process of preparing a compound of the formula

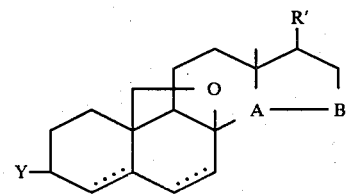

wherein Y is selected from the group consisting of α-OH, β-OH, H, =O, O—acyl and O—tetrahydropyranyl; A and B represent 14- and 15- carbon atoms, respectively, which are either linked by a double bond or an α-oxido bridge or have a hydroxy group, or acetoxy group or halogen atom in the 14β- or 14α-positions, in which case B is a methylene group; wherein the dotted lines represent optional double bonds in the 4(5) and/or 6(7) positions, and R' is selected from the group consisting of

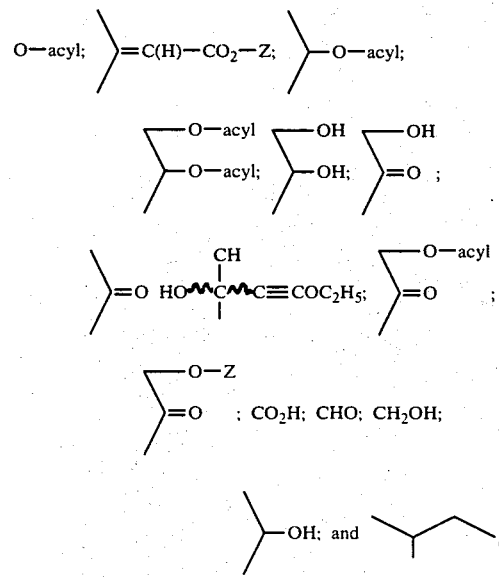

wherein Z is tetrahydropyranyl, lower alkyl, or a substituted methyl, wherein the substituent is selected from the group consisting of phenyl, halogen, methoxy, $CH_2$=CH and HC≡C; acyl represents a group selected from those consisting of formyl, acetyl, tri-lower-alkyl acetyls, wherein the lower alkyl group is methyl or ethyl, monohalo acetyls and trihalo acetyls, and in the case of AB-ring being a saturated 8,19-oxido 5α- and 5β-androst-14-enes and AB-ring saturated 21-unsubstituted 8,19-oxido 5α-pregn-14-enes, Y is H only, which process is selected from the group consisting of:
(a) treating a compound of the Formula II

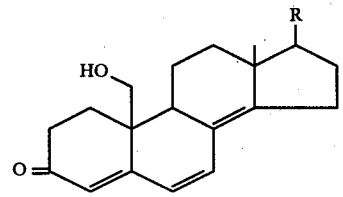

wherein R is as defined above, with a peracid, to form a mixture of compounds of the Formulae IIIa, IIIb or I, where Y' is O= and R is as defined above:

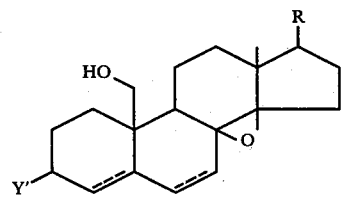

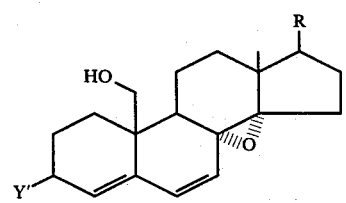

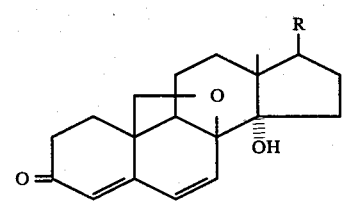

if desired separating compound IIIa thus obtained from the above mixture and treating the latter compound with an acid to form a 14β-hydroxy-3-ketone of Formula I, as follows:

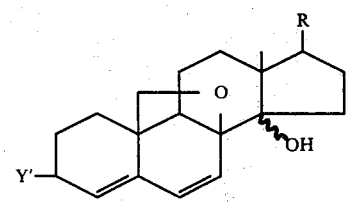

where Y' is O=; similarly separating the α-epoxide IIIb and treating it with an acid to form a 14α-hydroxy-3-ketone of the above formula I;
(b) treating a compound of the Formula IV

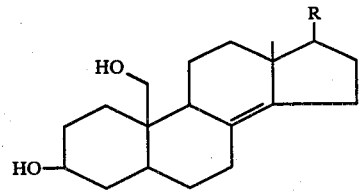
(IV)

wherein R is as defined above, with a peracid to form a mixture of compounds of the formulae

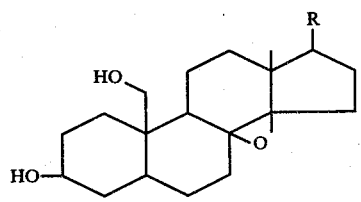
(V)

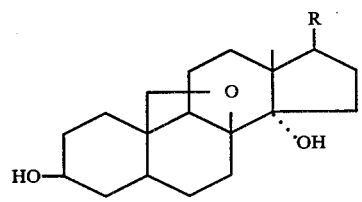

in which R is as defined above; if desired, separating from said mixture said compound of said Formula V, and treating said compound of Formula V under catalytic hydrogenation conditions or with an acid to form a compound of the Formula I as follows:

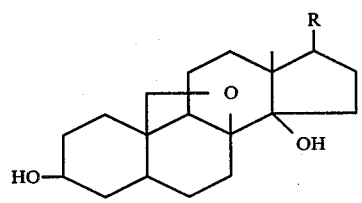
(I)

(c) epoxidizing a compound of the formula

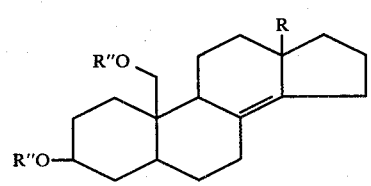
(VI)

wherein R is as defined above and R" is acyl, preferably O=C—H, O=C—Cl, O=C—CH$_3$, O=C—CH$_2$ halogen, O=C—CH (halogen)$_2$, O=C—C— (halogen)$_3$, O=C—C(CH$_3$)$_3$, O=C—O—CH$_2$—phenyl, O=C—O—C(CH$_3$)$_3$, into a mixture of compounds of the Formulae VII and VIII

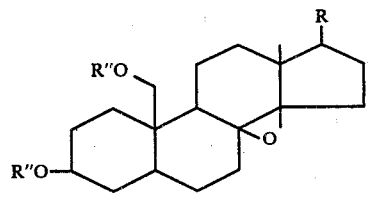
(VII)

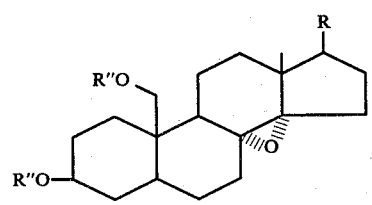
(VIII)

in which R' and R" are as defined above, separating from said mixture said compounds VII and VIII, and, in the case of the compound of the Formula VII, treating the latter with a base to form the compound of the Formula V and subsequently subjecting the latter to hydrogenation conditions to form a compound of the Formula I as follows:

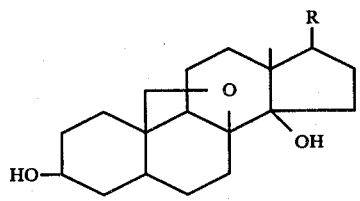
(I)

in the case of the compound of the Formula VIII, subjecting the latter to successive base-acid treatment to yield a compound of formula:

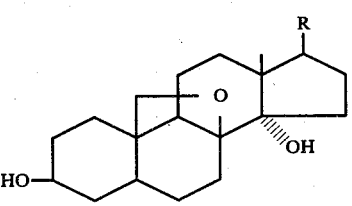
(I)

(d) epoxidizing a compound of the Formula IX

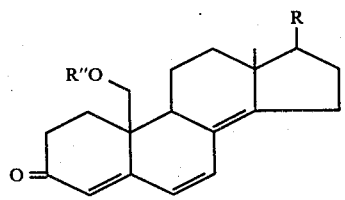
(IX)

wherein R" is as defined above to form a compound of the Formula X

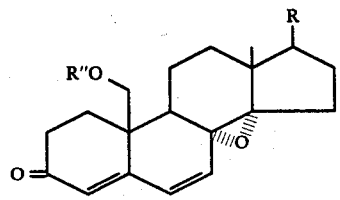

(X)

wherein R and R'' are as defined above; and treating the latter compound with a base and then with an acid to form a compound of the Formula I, as follows:

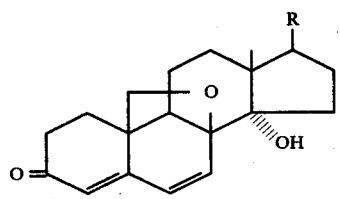

(e) oxidizing a compound of the Formula XI

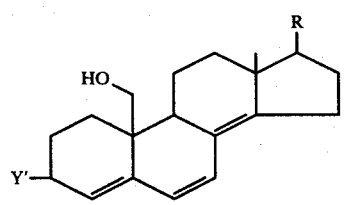

(XI)

wherein R is as defined above and Y' is OH or O=, to form a compound of the Formula I as follows

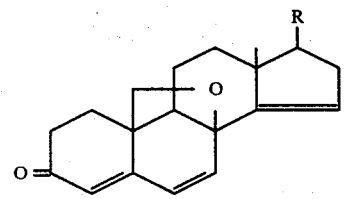

and (f) oxidizing a compound of the Formula XII

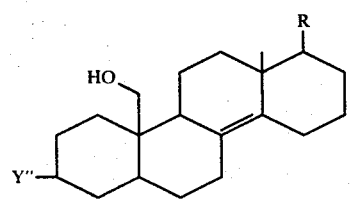

(XII)

wherein R is as defined above and Y'' is OH, O—acyl or =O to form a compound of the Formula I as follows:

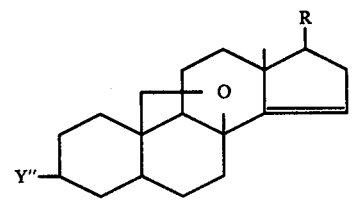

(I)

(g) epoxidizing a compound of the Formula XV

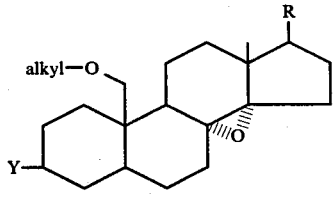

(XV)

wherein Y and R are as defined above, and alkyl is preferably tetrahydropyranyl, benzyl, allyl and propargyl, into a compound of Formula XVI

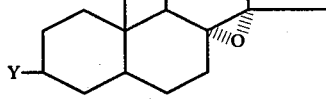

(XVI)

and subsequently subjecting the latter to hydrogenation conditions to form a compound of Formula I as follows:

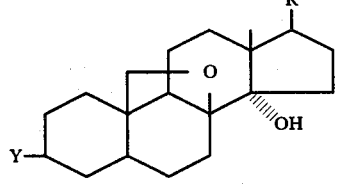

(I);

wherein Y and R are as defined above, (h) epoxidizing a compound of Formula XVII

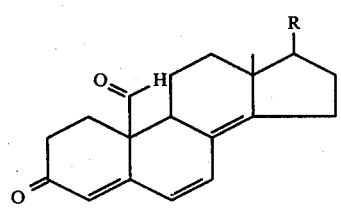

(XVII)

wherein R is as defined above, into a compound of Formula XVIII

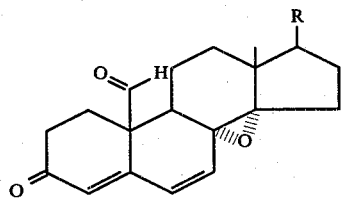
(XVIII)

and subsequently subjecting the latter to reducing conditions to form a compound of Formula I as follows:

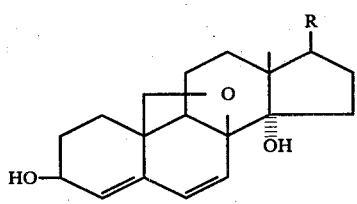
(I)

wherein R is as defined above.

2. A process of preparing a compound of the formula

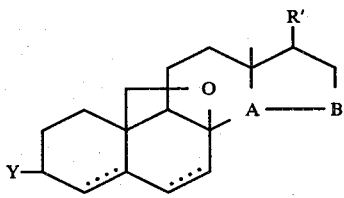
(Ia)

wherein Y, A and B are as defined in claim 1, and R' is selected from the group consisting of O—acyl; O—Z; OH; O;

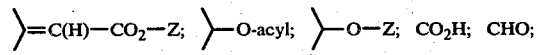

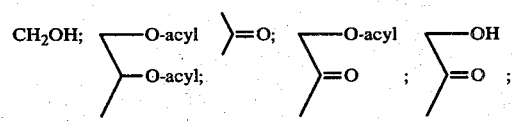

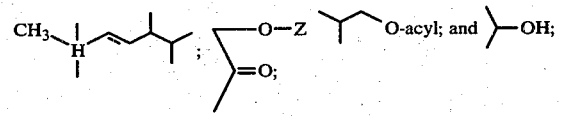

wherein Z and acyl are as defined in claim 1, which process comprises:

(a) treating a 19-hydroxy-8(14)-ene compound of the formula

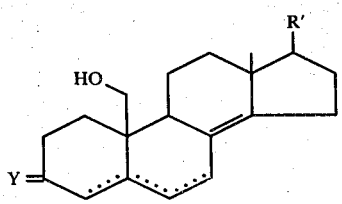

wherein Y, R' and the dotted lines represent optional double bonds in position 4(5), 5(6) and/or 6(7), with a peracid to form a mixture of the Formulae IIIa, IIIb and I

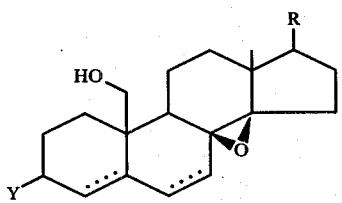
(IIIa)

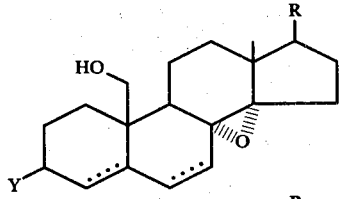
(IIIb)

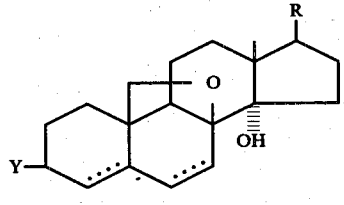
(I)

(b) and treating the compounds IIIa or IIIb with an acid to form a 14β or a 14α-hydroxy-8,19-oxide of Formula I below

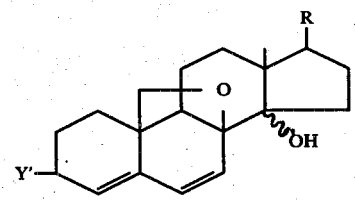
(I)

where the wavy line indicates that the 14-hydroxy is either in the β- or α-position.

3. A process as defined in claim 1(a) wherein the reaction is carried out using a non-polar solvent.

4. A process as defined in claim 1(c) wherein the reaction is carried out using a peracid, and wherein the hydrolysis is carried out using a base compound.

5. A process as defined in claim 1(e) wherein the process is carried out using lead tetraacetate or activated manganese dioxide.

6. A process as defined in claim 1(d) wherein the epoxidizing reaction is carried out using a peracid.

7. A process as defined in claim 1(f) wherein the compound of formula XII is initially halogenated.

8. A process as defined in claim 1(g) or 1(h) wherein the epoxidation is carried out using a peracid.

9. A 17-acyloxy compound of the formula

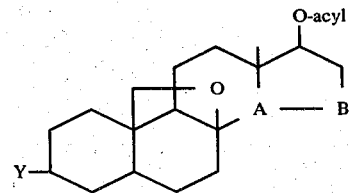

wherein acyl is formyl, acetyl or tri-lower alkyl with alkyl being methyl or ethyl; wherein Y is α or β-OH, H, O—tetrahydropyranyl, =O or O—acyl (acyl being as above-defined); and A—B is C=CH, C(OH)—CH₂,

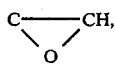

C(acetoxy)—CH₂ or C(Br)—CH₂ and the Δ2, Δ4 and Δ6 dehydro analogs thereof.

10. A 20-acyloxy compound of the formula

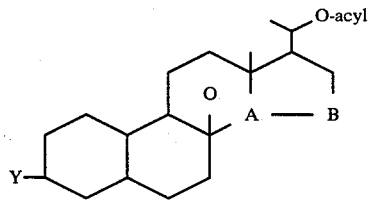

wherein acyl is formyl, acetyl or tri-lower alkyl with alkyl being methyl or ethyl; wherein Y is α or β-OH, H, O—tetrahydropyranyl, =O or O—acyl (acyl being as above-defined); and A-B is C=CH, C(OH)—CH₂,

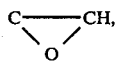

C(acetoxy)—CH₂ or C(Br)—CH₂ and the Δ2, Δ4 and Δ6 dehydro analogs thereof.

11. A 20-keto compound of the formula

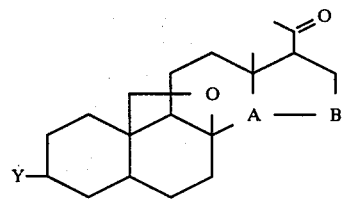

wherein Y is α or β-OH, H, O—tetrahydropyranyl, =O, or O—acyl, wherein acyl is formyl, acetyl or tri-lower alkyl with alkyl being methyl or ethyl; and A—B is C=CH, C(OH)—CH₂,

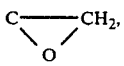

C(acetoxy)—CH₂ or C(Br)—CH₂ and the Δ4 and Δ6 dehydro analogs thereof.

12. A 21-oxygenated-20-keto compound of the formula

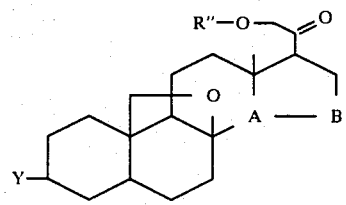

wherein R″ is H, lower alkyl, lower acyl, wherein acyl is formyl, acetyl or tri-lower alkyl with alkyl being methyl or ethyl, Y is OH or acetoxy and A—B is C=CH.

13. A 20-OH compound of the formula

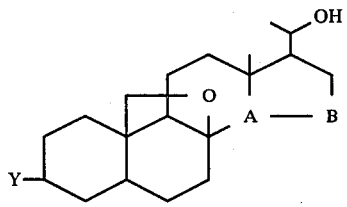

wherein Y is OH, tetrahydropyranyl or H and A—B is OH or C=CH, and the corresponding 20ε-hydroxy-20ε-ethoxyethynyl and 21-hydroxy analogues thereof.

14. A compound of the formula

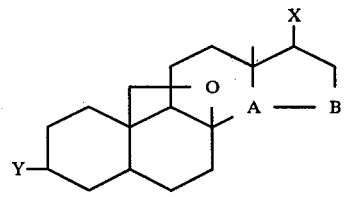

wherein X is COOH or CH₂OH, Y is H and A—B is C=CH.

15. A compound as defined in claim 9 wherein Y is selected from the group consisting of hydroxy, hydrogen and keto.

16. A compound as defined in claim 10, wherein Y is selected from the group consisting of hydroxy, hydrogen or keto.

17. A process as defined in claim 1(a) comprising the further step of reducing 8β,14β-oxido- or 8α,14α-oxido-4,6-dien-3-ones IIIa or IIIb to the corresponding 3-alcohols of the respective formulae IIIa or IIIb, Y' being OH, and subsequently subjecting the latter 8,14-oxides to acid treatment to form the respective 3,14β- and 3,14α-hydroxy-8,19-oxido-4,6-dienes of the Formula I.

18. A compound as defined in claim 10, wherein the compound is a 5β-H compound.

19. A compound as defined in claim 12, wherein the compound is a 5α-H compound.

20. A compound as defined in claim 11, said compound being a 3-H compound.

21. A compound as defined in claim 12, said compound being a 3-H compound.

22. A compound as defined in claim 11, said compound being a 5β-H compound.

23. A compound as defined in claim 12, said compound being a 5β-H compound.

24. A compound as defined in claim 9, said compound being 3β-acetoxy-14β-hydroxy-8,19-oxido-17β-pivaloxy-5α-androstane.

25. A compound as defined in claim 9, said compound being 14β-hydroxy-8,19-oxido-17β-pivaloxyandrosta-4,6-dien-3-one.

26. A compound as defined in claim 9, said compound being 3β,14β-dihydroxy-8,19-oxido-17β-pivaloxyandrosta-4,6-diene.

27. A compound as defined in claim 9, said compound being 3β,14β-hydroxy-8,19-oxido-17β-pivaloxy-5α-androstane.

28. A compound as defined in claim 9, said compound being 14-bromo-3β-hydroxy-8,19-oxido-17β-pivaloxy-5α-androstane.

29. A compound as defined in claim 9, said compound being 3β-hydroxy-8,19-oxido-20β-pivaloxy-5α-pregn-14-ene.

30. A compound as defined in claim 9, said compound being 8,19-oxido-20β-pivaloxy-5α-pregn-14-en-3β-yl.

31. A compound as defined in claim 9, said compound being 20β-hydroxy-8,19-oxido-5α-pregn-14-en-3β-yl.

32. A compound as defined in claim 11, said compound being 20-oxo-8,19-oxido-5α-pregn-14-en-3β-yl.

33. A compound as defined in claim 12, said compound being 21-acetoxy-3β-hydroxy-8,19-oxido-5α-pregn-14-en-20-one.

34. A compound as defined in claim 12, said compound being 3β,21-diacetoxy-8,19-oxido-5α-pregn-14-en-20-one.

35. A compound as defined in claim 9, said compound being 3β-acetoxy-8,19; 14,15-dioxido-17β-pivaloxy-5α-pregnane.

36. A compound as defined in claim 9, said compound being 8,19-oxido-17β-pivaloxyandrosta-4,6,14-trien-3-one.

37. A compound as defined in claim 10, said compound being 8,19-oxido-20β-pivaloxy pregn-4,6,14-trien-3-one.

38. A compound as defined in claim 10, said compound being 8,19-oxido-20β-pivaloxy-pregna-4,14-dien-3-one.

39. A compound as defined in claim 10, said compound being 8,19-oxido-20β-pivaloxy-5β-pregn-14-en-3-one.

40. A compound as defined in claim 10, said compound being 14β-hydroxy-8,19-oxido-20β-pivaloxy-pregna-4,6-dien-3-one.

41. A compound as defined in claim 10, said compound being 3β-acetoxy-8,19-oxido-5α-pregn-14-en-20-one.

42. A compound as defined in claim 11, said compound being 3β-hydroxy-8,19-oxido-5α-pregn-14-en-20-one tetrahydropyranyl ether.

43. A compound as defined in claim 11, said compound being 3β-hydroxy-8,19-oxido-5α-pregn-14-en-20-one.

44. A compound as defined in claim 10, said compound being 3β-acetoxy-8,19-oxido-20β-pivaloxy-5α-pregn-14-ene.

45. A compound as defined in claim 13, said compound being 3β,20β-dihydroxy-8,19-oxido-5α-preg-14-ene.

46. A compound as defined in claim 10, said compound being 3β,14β-dihydroxy-8,19-oxido-20β-pivaloxypregna-4,6-diene.

47. A compound as defined in claim 10, said compound being 3β,14β-dihydroxy-8,19-oxido-20β-pivaloxy-5α-pregnane.

48. A compound as defined in claim 10, said compound being 3β,14β-dihydroxy-8,19-oxido-20β-pivaloxy-5α-pregnane 3-pyranyl ether.

49. A compound as defined in claim 13, said compound being 3β,14β,20β-trihydroxy-8,19-oxido-5α-pregnane 3-tetrahydropyranyl ether.

50. A compound as defined in claim 11, said compound being 3β,14β-dihydroxy-8,19-oxido-5α-pregnan-20-one 3-tetrahydropyranyl ether.

51. A compound as defined in claim 11, said compound being 3β-acetoxy-14β-hydroxy-8,19-oxido-5α-pregnan-20-one.

52. A compound as defined in claim 13, said compound being 3β,14β,20-trihydroxy-20-ethoxyethinyl-8,19-oxido-5α-pregnane.

53. 3β-acetoxy-14β-hydroxy-8,19-oxido-5α-norchol-20-enic acid ethyl ester.

54. A compound as defined in claim 12, said compound being 3β,21-dihydroxy-8,19-oxido-5α-pregn-14-en-20-one.

55. A compound as defined in claim 12, said compound being 3β-acetoxy-21-hydroxy-8,19-oxido-5α-pregn-14-en-20-one.

56. A compound as defined in claim 12, said compound being 3β-acetoxy-21-methoxy-5α-pregn-14-en-20-one.

57. A compound as defined in claim 10, said compound being 14β-hydroxy-20β-pivaloxy-8,19-oxido-5α-pregnane.

58. A compound as defined in claim 11, said compound being 8,19-oxido-5α-pregn-14-en-20-one.

59. A compound as defined in claim 12, said compound being 21-acetoxy-8,19-oxido-5α-pregn-14-en-20-one.

60. A compound as defined in claim 12, said compound being 21-methoxy-8,19-oxido-5α-pregn-14-en-20-one.

61. A compound as defined in claim 10, said compound being 8,19-oxido-20β-pivaloxy-5α-pregn-14-en-3-one.

62. A compound as defined in claim 12, said compound being 21-hydroxy-8,19-oxido-5α-pregn-14-en-20-one.

63. A compound as defined in claim 14, said compound being 8,19-oxido-5α-androst-14-en-17β-carboxylic acid.

64. A compound as defined in claim 14, said compound being 17β-hydroxymethyl-8,19-oxido-5α-androst-14-ene.

65. A compound as defined in claim 13, said compound being 20, 21-dihydroxy-8,19-oxido-5α-pregn-14-ene.

66. A compound as defined in claim 9, said compound being 17β-formyl-8,19-oxido-5α-androst-14-ene.

67. A compound as defined in claim 14, said compound being 17β-hydroxymethyl-8,19-oxido-5α-androst-14-ene.

68. A compound as defined in claim 13, said compound being 14β,20β-dihydroxy-8,19-oxido-5α-pregnane.

69. A compound as defined in claim 11, said compound being 14β-hydroxy-8,19-oxido-5α-pregnan-20-one.

70. A compound as defined in claim 13, said compound being 14β,20ε-dihydroxy-20ε-ethyoxyethynyl-8,19-oxido-5α-pregnane.

71. A compound as defined in claim 13, said compound being 14β, 20ε-dihydroxy-20ε-ethoxyethynyl-8,19-oxido-5β-pregnane.

72. A compound as defined in claim 10, said compound being 8,19-oxido-20β-pivaloxy-5β-pregn-14-ene.

73. A compound as defined in claim 13, said compound being 20β-hydroxy-8,19-oxido-5β-pregn-14-ene.

74. A compound as defined in claim 11, said compound being 8,19-oxido-5β-pregn-14-en-20-one.

75. A compound as defined in claim 11, said compound being 20β-hydroxy-8,19-oxido-14-ene-5β-pregn-8(14)-ene.

76. A compound as defined in claim 11, said compound being 21-methoxy-8,19-oxido-5β-pregn-14-en-20-one.

77. A compound as defined in claim 11, said compound being 21-hydroxy-8,19-oxido-5β-pregn-14-en-20-one.

78. A compound as defined in claim 10, said compound being 8,19-oxido-14β-hydroxy-20β-pivaloxy-5β-pregnane.

79. A compound as defined in claim 11, said compound being 14β,20β-dihydroxy-8,19-oxido-5β-pregnane.

80. A compound as defined in claim 11, said compound being 14β-hydroxy-8,19-oxido-5β-pregnan-20-one.

81. A compound as defined in claim 9, wherein acyl represents a 20β-pivaloxy group, A—B represents a C=CH group and Y represents and α-H or α-OH group.

82. A compound as defined in claim 81 wherein Y represents an O—tetrahydropyranal group.

83. A compound as defined in claim 81, wherein Y represents a β-OH group.

84. A compound as defined in claim 81, wherein Y represents an acetate group.

85. A compound as defined in claim 13, wherein A—B represents a C=CH group and Y represents an α-H or α-OH group.

86. A compound as defined in claim 11, wherein A—B represents a C=CH group, and Y represents an α-H or α-OH group.

87. A compound as defined in claim 10, wherein A—B represents a C=CH group, and Y represents an α-H or α-OH group.

88. A compound as defined in claim 12, wherein R″ is OH, A—B represents a C=CH group, and Y represents an α-H or α-OH group.

89. Ethyl 14β-hydroxy-8,19oxido-5α or 5β-norchol-20(22)-enate.

* * * * *